US011204356B2

(12) United States Patent
Feldschuh et al.

(10) Patent No.: US 11,204,356 B2
(45) Date of Patent: Dec. 21, 2021

(54) BLOOD VOLUME ANALYSIS WITH VOLUME-AWARE BLOOD COMPONENT MEASURES AND TREATMENT

(71) Applicant: DAXOR CORP., New York, NY (US)

(72) Inventors: Jonathan Feldschuh, Jackson Heights, NY (US); Joseph Feldschuh

(73) Assignee: DAXOR CORP., New York, NY (US)

( * ) Notice: Subject to any disclaimer, the term of this patent is extended or adjusted under 35 U.S.C. 154(b) by 999 days.

(21) Appl. No.: 15/881,841

(22) Filed: Jan. 29, 2018

(65) Prior Publication Data
US 2018/0217168 A1 Aug. 2, 2018

Related U.S. Application Data

(60) Provisional application No. 62/451,813, filed on Jan. 30, 2017.

(51) Int. Cl.
| | |
|---|---|
| *G01N 33/80* | (2006.01) |
| *A61B 5/15* | (2006.01) |
| *G01N 33/60* | (2006.01) |
| *G01N 33/72* | (2006.01) |
| *G01N 33/68* | (2006.01) |
| *G16H 10/40* | (2018.01) |
| *G01N 35/00* | (2006.01) |
| *G01N 33/49* | (2006.01) |
| *A61M 1/34* | (2006.01) |
| *G16H 20/00* | (2018.01) |
| *A61B 5/155* | (2006.01) |

(52) U.S. Cl.
CPC .............. *G01N 33/80* (2013.01); *A61B 5/15* (2013.01); *G01N 33/49* (2013.01); *G01N 33/60* (2013.01); *G01N 33/68* (2013.01); *G01N 33/726* (2013.01); *G01N 35/00584* (2013.01); *G01N 35/00613* (2013.01); *G16H 10/40* (2018.01); *A61B 5/155* (2013.01); *A61M 1/341* (2014.02); *A61M 1/3496* (2013.01); *A61M 2202/0429* (2013.01); *A61M 2230/207* (2013.01); *G01N 2035/00653* (2013.01); *G01N 2333/76* (2013.01); *G16H 20/00* (2018.01)

(58) Field of Classification Search
None
See application file for complete search history.

(56) References Cited

U.S. PATENT DOCUMENTS

| | | | |
|---|---|---|---|
| 5,024,231 | A | 6/1991 | Feldschuh et al. |
| 5,529,189 | A | 6/1996 | Feldschuh |
| 6,299,583 | B1 | 10/2001 | Eggers et al. |
| 6,416,736 | B1 | 7/2002 | Bepperling et al. |
| 6,485,427 | B1 | 11/2002 | Lee et al. |
| 6,718,190 | B2 | 4/2004 | Krivitski et al. |
| 6,740,036 | B1 | 5/2004 | Lee et al. |
| 6,757,554 | B2 | 6/2004 | Rubinstein et al. |
| 7,590,437 | B2 | 9/2009 | Rubinstein et al. |
| 7,611,470 | B2 | 11/2009 | Rubinstein et al. |
| 8,082,016 | B2 | 12/2011 | Rubinstein et al. |
| 8,337,444 | B2 | 12/2012 | Rubinstein et al. |
| 8,535,234 | B2 | 9/2013 | Sugo |
| 8,551,342 | B2 | 10/2013 | Moissl et al. |
| 8,556,846 | B2 | 10/2013 | O'Mahony et al. |
| 8,591,428 | B2 | 11/2013 | Sugo |
| 9,002,656 | B2 | 4/2015 | Feldschuh et al. |
| 9,002,657 | B2 | 4/2015 | Feldschuh et al. |
| 9,283,315 | B2 | 3/2016 | Dam |
| 9,526,893 | B2 | 12/2016 | Averina et al. |
| 2008/0015486 | A1 | 1/2008 | Zhang et al. |
| 2010/0268101 | A1 | 10/2010 | Sugo |
| 2014/0121544 | A1 | 5/2014 | Sugo et al. |
| 2016/0296688 | A1 | 10/2016 | Boggs et al. |

OTHER PUBLICATIONS

Feldschuh J et al., "Prediction of the Normal Blood Volume, Relation of Blood Volume to Body Habitus," vol. 56, No. 4, Oct. 1977, pp. 605-612.
Liumbruno G et al., "Recommendations for the transfusion of red blood cells," Blood Transfus, 2009; 7: 49-64.
Nijboer J M M et al., "Myth or Reality: Hematocrit and Hemoglobin Differ in Trauma," J Trauma, 2007;62(5):1310-2.
Qaseem A et al., "Treatment of Anemia in Patients With Heart Disease: A Clinical Practice Guideline From the American College of Physicians," Ann Intern Med., 2013; 159:770-779.
Saltzberg M T, "Blood Volume Analysis Coupled with Ultrafiltration in the Management of Congestive Heart Failure-Guided Therapy to Achieve Euvolemia," US Cardiology, 2010;7(1):72-5.
Takanishi D M et al., "Peripheral Blood Hematocrit in Critically Ill Surgical Patients: An Imprecise Surrogate of True Red Blood Cell Volume," Anesth Analg 2008; 106:1808-12.
Carson J L et al., "Clinical Practice Guidelines From the AABB: Red Blood Cell Transfusion Thresholds and Storage," JAMA, 2016; 316(19):2025-2035, Abstract.
Pillon L et al., "Peripheral Blood Hematocrit Is a Poor Surrogate for Red Blood Cell Volume in Patients with Volume Excess or Depletion," Poster, National Kidney Foundation Conference, 2009.
Manzone T et al., "Normalized Hematocrit" from Blood Volume Analysis Offers Enhanced Accuracy over Peripheral Hematocrit in Assessment of Red Blood Cell Volume, Poster. Also in J. Nuc. Med, May 2010, vol. 51, Supplement 2, p. 1676.

*Primary Examiner* — G Steven Vanni
(74) *Attorney, Agent, or Firm* — Amster, Rothstein & Ebenstein LLP

(57) ABSTRACT

Methods and systems are presented for analyzing the blood of a living being. Equations are presented for volume-aware extension of the concept of Hematocrit. A method for calculating these volume-aware measures and using said measures to evaluate and guide possible treatments is described. A system comprising an automated analyzer and a processor and other components is described which can carry out said calculations. Methods of treatment for volume abnormalities are described which are guided by the volume-aware Hct measures. In one exemplary embodiment, a method of treatment for plasma volume excess using ultrafiltration is described. In another exemplary embodiment, a method of treatment for red cell volume excess using erythrocytapheresis is described.

20 Claims, 22 Drawing Sheets

|                                               | Patient Result | Normal Female |
|-----------------------------------------------|:--------------:|:-------------:|
| peripheral venous Hct (pHct)                  | 34.8%          | 37-41%        |
| fluid corrected Hct (fHct)                    | 41.9%          | 37-41%        |
| venesection corrected Hct (vHct)              | 34.0%          | 37-41%        |
| red cell volume corrected Hct (rHct)          | 33.7%          | 37-41%        |
| red cell total blood volume corrected Hct (tHct) | 19.3%       | 37-41%        |

FIG. 9

Patient Demographics

| | | |
|---|---|---|
| Patient Name: ▓▓▓ | DOB: ▓▓▓ | Analyzed On: ▓▓▓ |
| ID: ▓▓▓ | Gender: Female | Age: 68 |
| ACCESSION: - | Height: 150.00 cm | Analyst: AH |
| Referring MD: ▓▓▓ | Weight: 113.80 kg | Injectate Lot: V160610-809 |
| CC: - | Deviation from Ideal Weight: +131.9% | LOCATION: - |
| Comments: | | |

Blood Volume Analysis Results

| | BVA Result | Patient Ideal | Deviation From Ideal | Excess/Deficit % |
|---|---|---|---|---|
| Total Blood Volume | 6185 mL | 5137 mL | +1048 mL | +20.4% Moderate Excess |
| Red Blood Cell Volume | 1939 mL | 1851 mL | +88 mL | +4.8% Normal Excess |
| Plasma Volume | 4246 mL | 3286 mL | +960 mL | +29.2% Severe Excess |

*Blood Volume Interpretation Guideline*

| | Normal | Mild | Moderate | Severe | Extreme |
|---|---|---|---|---|---|
| BV, PV Deviation (± %): | 0 to 8 | >8 to 16 | >16 to 24 | >24 to 32 | >32 |
| RCV Deviation (± %): | 0 to 10 | >10 to 20 | >20 to 30 | >30 to 40 | >40 |

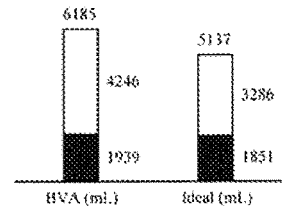

Additional Analysis

Hematocrit Analysis

| | Patient Result | Normal Female |
|---|---|---|
| peripheral venous Hct (pHct) | 34.8% | 37-41% |
| fluid corrected Hct (fHct) | 41.9% | 37-41% |
| venesection corrected Hct (vHct) | 34.0% | 37-41% |
| red cell volume corrected Hct (rHct) | 33.7% | 37-41% |
| red cell total blood volume corrected Hct (tHct) | 19.3% | 37-41% | mL/kg Analysis

| | Patient Result | Patient Ideal |
|---|---|---|
| Total Volume | 54.3 | 45.1 |
| Plasma Volume | 37.3 | 28.9 |
| RBC Volume | 17.0 | 16.3 |

Albumin Transudation Analysis/Slope (%/min)

| Patient Result | Reference Range |
|---|---|
| 0.21 | Normal: 0 to 0.4 |
| | High: 0.4 to 0.5 |
| | Unusually High: >0.5 |

FIG. 10

| State | Blood Volume (BV) | Red Cell Volume (RCV) | Plasma Volume (PV) | Example Peripheral Hct (pHct), male | Example fluid-corrected Hct (fHct), male | Other important volume corrected measures | Comments |
|---|---|---|---|---|---|---|---|
| Normal | Normal | Normal | Normal | 45% | 45% | | |
| Anemia (with normal BV) | Normal | Low | High | 35% | 35% | $w_iHct$, rHct | Only in patents with a normal BV does pHct = fHct; Correcting deficit of red cells |
| Compensated polycythemia | Normal | High | Low | 51% | 51% | vHct, rHct | Correcting excess of red cells |
| Uncompensated polycythemia | High | High | Normal | 47% | 51% | vHct, rHct, tHct | In Polycythemia vera, lack of compensatory decrease in PV results in lack of recognition of full expansion of the Red Cell Volume. |
| Severe polycythemia | High | Very High | Moderately decreased | 51% | 61% | vHct, rHct, tHct | Extent of RCV expansion is underestimated by pHct; Phlebotomy guided by value of vHct |
| Congestive heart failure | High | Moderately Expanded | Disproportionally Expanded | 42% | 51% | vHct | vHct and fHct help to guide use of phlebotomy and diuretics; serial blood volume measurements may be helpful |
| Mild Hypovolemia | Moderately Low | Moderately Low | Less decreased proportionally than RCV | 39% | 33% | $w_iHct$, rHct, tHct | Seen in post-op surgery particularly with decreased albumin. |
| Moderate Hypovolemia | Low | Low | Less decreased proportionally than RCV | 34% | 28% | $w_iHct$, rHct, tHct | pHct underestimates true extent of Blood volume deficit, primarily red cells. |
| Severe Hypovolemia | Very Low | Extremely Low | Less decreased proportionally than RCV | 29% | 22% | $w_iHct$, rHct, tHct | Extremely unstable post-op patient's severity of deficit masked by pHct |

FIG. 11

Deviation from iHct:

| | -15% | -10% | -5% | 0% | 5% | 10% | 15% |
|---|---|---|---|---|---|---|---|
| Male | 38.25% | 40.50% | 42.75% | 45.00% | 47.25% | 49.50% | 51.75% |
| Female | 34.00% | 36.00% | 38.00% | 40.00% | 42.00% | 44.00% | 46.00% |

| description | VERY LOW | LOW | moderately low | normal | moderately high | HIGH | VERY HIGH |
|---|---|---|---|---|---|---|---|

FIG. 12

| ID | Sex | pHct | iHct | edBV | edRCV | edPV | fHct | wiHct | vHct | rHct | tHct |
|---|---|---|---|---|---|---|---|---|---|---|---|
| 224 | Male | 36.0% | 45.0% | -17.6% | -34.1% | -6.4% | 29.7% | 38.5% | 36.7% | 46.8% | 49.2% |
| 2401 | Male | 36.0% | 45.0% | +13.6% | -9.1% | +29.1% | 40.9% | 34.1% | 35.5% | 38.4% | 25.8% |
| 4501 | Male | 36.0% | 45.0% | +8.9% | -12.9% | +23.7% | 39.2% | 34.8% | 35.6% | 39.4% | 29.3% |
| 5253 | Male | 36.0% | 45.0% | -0.7% | -20.5% | +12.9% | 35.8% | 36.1% | 36.0% | 41.8% | 36.5% |
| 6884 | Male | 36.0% | 45.0% | +9.6% | -12.4% | +24.6% | 39.5% | 34.6% | 35.6% | 39.3% | 28.7% |
| 7346 | Male | 36.0% | 45.0% | +12.9% | -9.6% | +28.2% | 40.6% | 34.2% | 35.5% | 38.5% | 26.4% |
| 7898 | Male | 36.0% | 45.0% | +9.1% | -12.7% | +24.0% | 39.3% | 34.7% | 35.6% | 39.4% | 29.2% |
| 8285 | Male | 36.0% | 45.0% | +10.1% | -11.9% | +25.1% | 39.6% | 34.6% | 35.6% | 39.2% | 28.4% |
| 8558 | Male | 36.0% | 45.0% | +18.9% | -4.9% | +35.1% | 42.8% | 33.4% | 35.3% | 37.2% | 21.9% |
| 8562 | Male | 36.0% | 45.0% | +27.3% | +1.9% | +44.7% | 45.8% | 32.2% | 34.9% | 35.6% | 15.5% |
| 8767 | Male | 36.0% | 45.0% | +24.7% | -0.2% | +41.7% | 44.9% | 32.6% | 35.0% | 36.1% | 17.5% |
| 8842 | Male | 36.0% | 45.0% | +24.1% | -0.7% | +41.0% | 44.7% | 32.7% | 35.1% | 36.2% | 18.0% |
| 9496 | Male | 36.0% | 45.0% | +43.7% | +15.0% | +63.3% | 51.7% | 29.9% | 34.3% | 32.7% | 3.2% |
| 9519 | Male | 36.0% | 45.0% | +7.8% | -13.8% | +22.4% | 38.8% | 34.9% | 35.7% | 39.7% | 30.2% |
| 9550 | Male | 36.0% | 45.0% | +4.9% | -16.1% | +19.2% | 37.8% | 35.3% | 35.8% | 40.4% | 32.3% |
| 9651 | Male | 36.0% | 45.0% | -4.6% | -23.7% | +8.4% | 34.4% | 36.6% | 36.2% | 42.9% | 39.4% |
| 10220 | Male | 36.0% | 45.0% | +11.6% | -10.7% | +26.9% | 40.2% | 34.4% | 35.5% | 38.8% | 27.3% |
| 10484 | Male | 36.0% | 45.0% | -5.2% | -24.2% | +7.7% | 34.1% | 36.7% | 36.2% | 43.0% | 39.9% |
| 10602 | Male | 36.0% | 45.0% | +13.4% | -9.3% | +28.8% | 40.8% | 34.1% | 35.5% | 38.4% | 26.0% |
| 10715 | Male | 36.0% | 45.0% | +20.5% | -3.6% | +36.9% | 43.4% | 33.1% | 35.2% | 36.9% | 20.6% |
| 10872 | Male | 36.0% | 45.0% | +2.4% | -18.1% | +16.4% | 36.9% | 35.7% | 35.9% | 41.0% | 34.2% |
| 10996 | Male | 36.0% | 45.0% | +36.7% | +9.4% | +55.4% | 49.2% | 30.9% | 34.6% | 33.9% | 8.5% |
| 11282 | Male | 36.0% | 45.0% | -11.8% | -29.4% | +0.3% | 31.8% | 37.6% | 36.5% | 44.9% | 44.8% |
| 11780 | Male | 36.0% | 45.0% | +6.4% | -14.9% | +20.9% | 38.3% | 35.1% | 35.7% | 40.0% | 31.2% |
| 12060 | Male | 36.0% | 45.0% | -34.1% | -47.3% | -25.1% | 23.7% | 40.8% | 37.4% | 52.9% | 61.6% |
| 12349 | Male | 36.0% | 45.0% | +22.7% | -1.8% | +39.4% | 44.2% | 32.8% | 35.1% | 36.5% | 19.0% |
| 12435 | Male | 36.0% | 45.0% | -19.3% | -35.4% | -8.3% | 29.1% | 38.7% | 36.8% | 47.3% | 50.5% |
| 13437 | Male | 36.0% | 45.0% | -9.1% | -27.3% | +3.3% | 32.7% | 37.3% | 36.4% | 44.1% | 42.8% |
| 13528 | Male | 36.0% | 45.0% | -16.2% | -33.0% | -4.8% | 30.2% | 38.3% | 36.6% | 46.3% | 48.1% |
| 13558 | Male | 36.0% | 45.0% | +17.4% | -6.1% | +33.4% | 42.3% | 33.6% | 35.3% | 37.5% | 22.9% |
| 13610 | Male | 36.0% | 45.0% | -10.5% | -28.4% | +1.7% | 32.2% | 37.5% | 36.4% | 44.6% | 43.9% |
| 13838 | Male | 36.0% | 45.0% | +0.3% | -19.8% | +14.0% | 36.1% | 36.0% | 36.0% | 41.6% | 35.8% |
| 14383 | Male | 36.0% | 45.0% | +34.9% | +7.9% | +53.3% | 48.6% | 31.1% | 34.6% | 34.2% | 9.8% |
| 14384 | Male | 36.0% | 45.0% | +8.0% | -13.6% | +22.7% | 38.9% | 34.9% | 35.7% | 39.6% | 30.0% |
| 14707 | Male | 36.0% | 45.0% | +46.0% | +16.8% | +65.9% | 52.5% | 29.6% | 34.2% | 32.3% | 1.5% |

FIG. 13

| ID | Sex | pHct | iHct | edBV | edRCV | edPV | fHct | wiHct | vHct | rHct | tHct |
|---|---|---|---|---|---|---|---|---|---|---|---|
| 1465 | Female | 45.0% | 40.0% | -2.3% | +10.0% | -9.2% | 44.0% | 45.0% | 45.1% | 42.5% | 46.5% |
| 2058 | Female | 45.0% | 40.0% | -3.8% | +8.2% | -10.6% | 43.3% | 45.0% | 45.2% | 42.9% | 47.5% |
| 3259 | Female | 45.0% | 40.0% | +26.7% | +42.6% | +17.8% | 57.0% | 45.2% | 43.7% | 35.9% | 27.4% |
| 3513 | Female | 45.0% | 40.0% | +4.4% | +17.4% | -3.0% | 47.0% | 45.0% | 44.8% | 40.8% | 42.1% |
| 3907 | Female | 45.0% | 40.0% | -3.5% | +8.6% | -10.3% | 43.4% | 45.0% | 45.2% | 42.8% | 47.3% |
| 6463 | Female | 45.0% | 40.0% | -2.1% | +10.2% | -9.0% | 44.0% | 45.0% | 45.1% | 42.5% | 46.4% |
| 6731 | Female | 45.0% | 40.0% | +13.7% | +28.0% | +5.6% | 51.2% | 45.1% | 44.4% | 38.6% | 36.0% |
| 13372 | Female | 45.0% | 40.0% | +11.6% | +25.6% | +3.8% | 50.2% | 45.1% | 44.4% | 39.1% | 37.3% |
| 219 | Male | 45.0% | 45.0% | +12.4% | +12.4% | +12.5% | 50.6% | 44.4% | 44.4% | 41.9% | 36.8% |
| 968 | Male | 45.0% | 45.0% | +15.9% | +15.9% | +15.9% | 52.2% | 44.2% | 44.2% | 41.1% | 34.5% |
| 1012 | Male | 45.0% | 45.0% | -3.9% | -3.9% | -3.9% | 43.3% | 45.2% | 45.2% | 46.1% | 47.5% |
| 1151 | Male | 45.0% | 45.0% | +10.3% | +10.3% | +10.3% | 49.6% | 44.5% | 44.5% | 42.4% | 38.2% |
| 1483 | Male | 45.0% | 45.0% | -10.5% | -10.5% | -10.5% | 40.3% | 45.5% | 45.5% | 48.0% | 51.9% |
| 1694 | Male | 45.0% | 45.0% | +8.9% | +8.9% | +8.9% | 49.0% | 44.6% | 44.6% | 42.7% | 39.1% |
| 2116 | Male | 45.0% | 45.0% | +6.1% | +6.1% | +6.1% | 47.7% | 44.7% | 44.7% | 43.4% | 41.0% |
| 2307 | Male | 45.0% | 45.0% | -2.8% | -2.8% | -2.8% | 43.7% | 45.1% | 45.1% | 45.8% | 46.8% |
| 2310 | Male | 45.0% | 45.0% | +5.9% | +5.9% | +6.0% | 47.7% | 44.7% | 44.7% | 43.5% | 41.1% |
| 2511 | Male | 45.0% | 45.0% | +19.8% | +19.8% | +19.8% | 53.9% | 44.0% | 44.0% | 40.3% | 31.9% |
| 2512 | Male | 45.0% | 45.0% | +16.6% | +16.6% | +16.6% | 52.5% | 44.2% | 44.2% | 41.0% | 34.0% |
| 2513 | Male | 45.0% | 45.0% | +16.2% | +16.2% | +16.2% | 52.3% | 44.2% | 44.2% | 41.0% | 34.3% |
| 3017 | Male | 45.0% | 45.0% | +27.6% | +27.6% | +27.6% | 57.4% | 43.6% | 43.6% | 38.7% | 26.8% |
| 3157 | Male | 45.0% | 45.0% | +5.4% | +5.4% | +5.5% | 47.5% | 44.7% | 44.7% | 43.6% | 41.4% |
| 4374 | Male | 45.0% | 45.0% | -4.7% | -4.7% | -4.7% | 42.9% | 45.2% | 45.2% | 46.3% | 48.1% |
| 4381 | Male | 45.0% | 45.0% | -1.6% | -1.6% | -1.6% | 44.3% | 45.1% | 45.1% | 45.4% | 46.0% |
| 5173 | Male | 45.0% | 45.0% | -1.6% | -1.6% | -1.6% | 44.3% | 45.1% | 45.1% | 45.4% | 46.1% |
| 6044 | Male | 45.0% | 45.0% | +1.8% | +1.8% | +1.8% | 45.8% | 44.9% | 44.9% | 44.5% | 43.8% |
| 6045 | Male | 45.0% | 45.0% | -0.0% | -0.0% | -0.1% | 45.0% | 45.0% | 45.0% | 45.0% | 45.0% |
| 6046 | Male | 45.0% | 45.0% | -0.5% | -0.5% | -0.5% | 44.8% | 45.0% | 45.0% | 45.1% | 45.3% |
| 6047 | Male | 45.0% | 45.0% | +2.8% | +2.8% | +2.8% | 46.3% | 44.9% | 44.9% | 44.3% | 43.1% |
| 6846 | Male | 45.0% | 45.0% | +17.8% | +17.8% | +17.8% | 53.0% | 44.1% | 44.1% | 40.7% | 33.3% |
| 7177 | Male | 45.0% | 45.0% | -12.5% | -12.5% | -12.5% | 39.4% | 45.6% | 45.6% | 48.6% | 53.3% |
| 7243 | Male | 45.0% | 45.0% | +4.9% | +5.0% | +4.8% | 47.2% | 44.8% | 44.8% | 43.7% | 41.8% |
| 7311 | Male | 45.0% | 45.0% | -6.4% | -6.3% | -6.4% | 42.1% | 45.3% | 45.3% | 46.8% | 49.2% |
| 7328 | Male | 45.0% | 45.0% | -10.9% | -10.9% | -10.9% | 40.1% | 45.5% | 45.5% | 48.1% | 52.2% |
| 9643 | Male | 45.0% | 45.0% | +34.1% | +34.1% | +34.1% | 60.4% | 43.3% | 43.3% | 37.4% | 22.5% |
| 10272 | Male | 45.0% | 45.0% | +54.3% | +54.3% | +54.3% | 69.4% | 42.3% | 42.3% | 34.0% | 9.1% |
| 13773 | Male | 45.0% | 45.0% | +23.9% | +23.8% | +23.9% | 55.7% | 43.8% | 43.8% | 39.4% | 29.3% |
| 14172 | Male | 45.0% | 45.0% | -6.7% | -6.7% | -6.7% | 42.0% | 45.3% | 45.3% | 46.9% | 49.4% |

FIG. 14

| [002] Hct Measure | [003] Ideal [004] Volume Target | [005] Changing | [006] Additive Treatments | [007] Removal Treatments | [008] pHct change with Addition |
|---|---|---|---|---|---|
| fHct | Blood Volume | fluids | Plasma transfusion, albumin transfusion, IV fluids, oral rehydration, etc. | Diuretics, ultrafiltration, plasmapheresis, etc. | decreases |
| aHct | Plasma Volume | | | | |
| $w_b$Hct, $w_i$Hct | Blood Volume | whole blood | Whole blood transfusion; combined plasma and red cell transfusion | Not applicable | varies |
| vHct | Blood Volume | | Not applicable | Venesection | slightly decreases with venesection |
| $w_{70}$Hct | Blood Volume | packed red cells | Red blood cell transfusion with typical packed cells (Hct=70%) | Not applicable | increases |
| $r_{70}$Hct | Red Cell Volume | | | | |
| rHct | Red Cell Volume | red cells | Not applicable | Erythrocytapheresis, various drug treatments | increases |
| tHct | Blood Volume | | | | |
| iHct | BV, PV, and RCV | fluid and red cells | varies | varies | varies |

FIG. 15

```
===============================================================================================================
Patient 224:(Male)

Blood Volume:      Current = 5217 ml | Ideal = 6334 ml | Deviation = -1117 ml = -17.6% (moderate deficit)
Plasma Volume:     Current = 3525 ml | Ideal = 3766 ml | Deviation =  -241 ml =  -6.4% (normal deficit)
Red Cell Volume:   Current = 1692 ml | Ideal = 2568 ml | Deviation =  -876 ml = -34.1% (SEVERE DEFICIT)

Status             Hct measure        Intervention                                Volume Target
-----------------------------------------------------------------------------------------------------------
(VERY LOW)         pHct =  36.0% <- CURRENT VALUE
(Ideal)            iHct =  45.0% <- addition of  241 ml of fluids                 to achieve Ideal Plasma Volume
                                AND addition of  876 ml of red cells              to achieve Ideal Red Cell Volume
(normal)           r70Hct = 44.1% <- addition of 1251 ml of packed red cells      to achieve Ideal Red Cell Volume
(normal)           w70Hct = 43.4% <- addition of 1117 ml of packed red cells      to achieve Ideal Blood Volume
-----------------------------------------------------------------------------------------------------------
(LOW)              wiHct =  38.5% <- addition of 1117 ml of whole blood (iHct) to achieve Ideal Blood Volume
(VERY LOW)         aHct =   34.4% <- addition of  241 ml of fluids                to achieve Ideal Plasma Volume
(VERY LOW)         fHct =   29.7% <- addition of 1117 ml of fluids                to achieve Ideal Blood Volume
===============================================================================================================

===============================================================================================================
Patient 2401:(Male)

Blood Volume:      Current = 6400 ml | Ideal = 5634 ml | Deviation =   766 ml = +13.6% (mild excess)
Plasma Volume:     Current = 4324 ml | Ideal = 3350 ml | Deviation =   974 ml = +29.1% (SEVERE EXCESS)
Red Cell Volume:   Current = 2076 ml | Ideal = 2284 ml | Deviation =  -208 ml =  -9.1% (normal deficit)

Status             Hct measure        Intervention                                Volume Target
-----------------------------------------------------------------------------------------------------------
(VERY LOW)         pHct =  36.0% <- CURRENT VALUE
(Ideal)            iHct =  45.0% <- removal  of  974 ml of fluids                 to achieve Ideal Plasma Volume
                                AND addition of  208 ml of red cells              to achieve Ideal Red Cell Volume
-----------------------------------------------------------------------------------------------------------
(moderately low)   aHct =   42.5% <- removal  of  974 ml of fluids                to achieve Ideal Plasma Volume
(moderately low)   fHct =   40.9% <- removal  of  766 ml of fluids                to achieve Ideal Blood Volume
(VERY LOW)         r70Hct = 37.9% <- addition of  297 ml of packed red cells      to achieve Ideal Red Cell Volume
(VERY LOW)         vHct =   35.5% <- removal  of  766 ml of whole blood           to achieve Ideal Blood Volume
(VERY LOW)         tHct =   25.8% <- removal  of  766 ml of red cells             to achieve Ideal Blood Volume
===============================================================================================================
```

FIG. 16

```
===============================================================================================
Patient 4501:(Male)

Blood Volume:      Current = 6198 ml | Ideal = 5693 ml | Deviation =   505 ml = +8.9% (mild excess)
Plasma Volume:     Current = 4188 ml | Ideal = 3385 ml | Deviation =   803 ml = +23.7% (moderate excess)
Red Cell Volume:   Current = 2010 ml | Ideal = 2308 ml | Deviation =  -298 ml = -12.9% (mild deficit)

Status             Hct measure        Intervention                          Volume Target
-----------------------------------------------------------------------------------------------
(VERY LOW)         pHct =  36.0% <- CURRENT VALUE
(Ideal)            iHct =  45.0% <- removal  of  803 ml of fluids           to achieve Ideal Plasma Volume
                                 AND addition of  298 ml of red cells       to achieve Ideal Red Cell Volume
-----------------------------------------------------------------------------------------------
(moderately low)   aHct =  41.4% <- removal  of  803 ml of fluids           to achieve Ideal Plasma Volume
(LOW)              fHct =  39.2% <- removal  of  505 ml of fluids           to achieve Ideal Blood Volume
(LOW)              r70Hct = 38.7% <- addition of  426 ml of packed red cells to achieve Ideal Red Cell Volume
(VERY LOW)         vHct =  35.6% <- removal  of  505 ml of whole blood      to achieve Ideal Blood Volume
(VERY LOW)         tHct =  29.3% <- removal  of  505 ml of red cells        to achieve Ideal Blood Volume
===============================================================================================

===============================================================================================
Patient 8767:(Male)

Blood Volume:      Current = 6123 ml | Ideal = 4909 ml | Deviation =  1214 ml = +24.7% (SEVERE EXCESS)
Plasma Volume:     Current = 4137 ml | Ideal = 2919 ml | Deviation =  1218 ml = +41.7% (EXTREME EXCESS)
Red Cell Volume:   Current = 1986 ml | Ideal = 1990 ml | Deviation =    -4 ml = -0.2% (normal deficit)

Status             Hct measure        Intervention                          Volume Target
-----------------------------------------------------------------------------------------------
(VERY LOW)         pHct =  36.0% <- CURRENT VALUE
(Ideal)            iHct =  45.0% <- removal  of 1218 ml of fluids           to achieve Ideal Plasma Volume
                                 AND addition of    4 ml of red cells       to achieve Ideal Red Cell Volume
(normal)           aHct =  44.9% <- removal  of 1218 ml of fluids           to achieve Ideal Plasma Volume
(normal)           fHct =  44.9% <- removal  of 1214 ml of fluids           to achieve Ideal Blood Volume
-----------------------------------------------------------------------------------------------
(VERY LOW)         r70Hct = 36.0% <- addition of    6 ml of packed red cells to achieve Ideal Red Cell Volume
(VERY LOW)         vHct =  35.0% <- removal  of 1214 ml of whole blood      to achieve Ideal Blood Volume
(VERY LOW)         tHct =  17.5% <- removal  of 1214 ml of red cells        to achieve Ideal Blood Volume
===============================================================================================
```

FIG. 17

```
===============================================================================================================
Patient 12060:(Male)

Blood Volume:     Current = 3274 ml | Ideal = 4970 ml | Deviation = -1696 ml = -34.1% (EXTREME DEFICIT)
Plasma Volume:    Current = 2212 ml | Ideal = 2955 ml | Deviation =  -743 ml = -25.1% (SEVERE DEFICIT)
Red Cell Volume:  Current = 1062 ml | Ideal = 2015 ml | Deviation =  -953 ml = -47.3% (EXTREME DEFICIT)

Status             Hct measure     Intervention                                  Volume Target
---------------------------------------------------------------------------------------------------------------
(VERY LOW)         pHct =  36.0% <- CURRENT VALUE
(Ideal)            iHct =  45.0% <- addition of  743 ml of fluids               to achieve Ideal Plasma Volume
                                 AND addition of  953 ml of red cells           to achieve Ideal Red Cell Volume
---------------------------------------------------------------------------------------------------------------
(moderately high)  r70Hct = 48.3% <- addition of 1361 ml of packed red cells    to achieve Ideal Red Cell Volume
(moderately low)   wiHct =  40.8% <- addition of 1696 ml of whole blood (iHct)  to achieve Ideal Blood Volume
(HIGH)             w70Hct = 50.2% <- addition of 1696 ml of packed red cells    to achieve Ideal Blood Volume
(VERY LOW)         aHct =   29.3% <- addition of  743 ml of fluids              to achieve Ideal Plasma Volume
(VERY LOW)         fHct =   23.7% <- addition of 1696 ml of fluids              to achieve Ideal Blood Volume
===============================================================================================================

===============================================================================================================
Patient 14383:(Male)

Blood Volume:     Current = 6371 ml | Ideal = 4723 ml | Deviation = 1648 ml = +34.9% (EXTREME EXCESS)
Plasma Volume:    Current = 4305 ml | Ideal = 2808 ml | Deviation = 1497 ml = +53.3% (EXTREME EXCESS)
Red Cell Volume:  Current = 2066 ml | Ideal = 1915 ml | Deviation =  151 ml =  +7.9% (normal excess)

Status             Hct measure     Intervention                                  Volume Target
---------------------------------------------------------------------------------------------------------------
(VERY LOW)         pHct =  36.0% <- CURRENT VALUE
(Ideal)            iHct =  45.0% <- removal of 1497 ml of fluids                to achieve Ideal Plasma Volume
                                 AND removal of  151 ml of red cells            to achieve Ideal Red Cell Volume
(normal)           aHct =  47.1% <- removal of 1497 ml of fluids                to achieve Ideal Plasma Volume
---------------------------------------------------------------------------------------------------------------
(moderately high)  fHct =  48.6% <- removal of 1648 ml of fluids                to achieve Ideal Blood Volume
(VERY LOW)         vHct =  34.6% <- removal of 1648 ml of whole blood           to achieve Ideal Blood Volume
(VERY LOW)         rHct =  34.2% <- removal of  151 ml of red cells             to achieve Ideal Red Cell Volume
(VERY LOW)         tHct =   9.8% <- removal of 1648 ml of red cells             to achieve Ideal Blood Volume
===============================================================================================================
```

FIG. 18

```
===============================================================================
Patient 7177:(Male)

Blood Volume:     Current = 4762 ml | Ideal = 5443 ml | Deviation =  -681 ml = -12.5% (mild deficit)
Plasma Volume:    Current = 2830 ml | Ideal = 3236 ml | Deviation =  -406 ml = -12.5% (mild deficit)
Red Cell Volume:  Current = 1932 ml | Ideal = 2207 ml | Deviation =  -275 ml = -12.5% (mild deficit)

Status              Hct measure       Intervention                              Volume Target
-------------------------------------------------------------------------------------------------------
(normal)            pHct =  45.0% <- CURRENT VALUE
(Ideal)             iHct =  45.0% <- addition of  406 ml of fluids              to achieve Ideal Plasma Volume
                                  AND addition of  275 ml of red cells          to achieve Ideal Red Cell Volume
(normal)            wiHct = 45.6% <- addition of  681 ml of whole blood (iHct)  to achieve Ideal Blood Volume
-------------------------------------------------------------------------------------------------------
(moderately high)   r70Hct = 47.5% <- addition of  393 ml of packed red cells   to achieve Ideal Red Cell Volume
(moderately low)    aHct =   41.5% <- addition of  406 ml of fluids             to achieve Ideal Plasma Volume
(HIGH)              w70Hct = 49.1% <- addition of  681 ml of packed red cells   to achieve Ideal Blood Volume
(LOW)               fHct =   39.4% <- addition of  681 ml of fluids             to achieve Ideal Blood Volume
===============================================================================

===============================================================================
Patient 5173:(Male)

Blood Volume:     Current = 5221 ml | Ideal = 5306 ml | Deviation =  -85 ml = -1.6% (normal deficit)
Plasma Volume:    Current = 3104 ml | Ideal = 3155 ml | Deviation =  -51 ml = -1.6% (normal deficit)
Red Cell Volume:  Current = 2117 ml | Ideal = 2151 ml | Deviation =  -34 ml = -1.6% (normal deficit)

Status                  Hct measure       Intervention                          Volume Target
-------------------------------------------------------------------------------------------------------
(normal Hct & volumes)  pHct =  45.0% <- CURRENT VALUE
-------------------------------------------------------------------------------------------------------
(Ideal)                 iHct =  45.0% <- addition of  51 ml of fluids           to achieve Ideal Plasma Volume
                                      AND addition of  34 ml of red cells       to achieve Ideal Red Cell Volume
(normal)                wiHct = 45.1% <- addition of  85 ml of whole blood (iHct) to achieve Ideal Blood Volume
(normal)                r70Hct = 45.3% <- addition of  49 ml of packed red cells to achieve Ideal Red Cell Volume
(normal)                aHct =  44.6% <- addition of  51 ml of fluids           to achieve Ideal Plasma Volume
(normal)                w70Hct = 45.5% <- addition of  85 ml of packed red cells to achieve Ideal Blood Volume
(normal)                fHct =  44.3% <- addition of  85 ml of fluids           to achieve Ideal Blood Volume
===============================================================================
```

FIG. 19

```
===============================================================================
Patient 10272:(Male)

Blood Volume:      Current = 7940 ml | Ideal = 5145 ml | Deviation =  2795 ml = +54.3% (EXTREME EXCESS)
Plasma Volume:     Current = 4721 ml | Ideal = 3059 ml | Deviation =  1662 ml = +54.3% (EXTREME EXCESS)
Red Cell Volume:   Current = 3219 ml | Ideal = 2086 ml | Deviation =  1133 ml = +54.3% (EXTREME EXCESS)

Status             Hct measure      Intervention                              Volume Target
-------------------------------------------------------------------------------------------------------
(normal)           pHct =  45.0% <- CURRENT VALUE
(Ideal)            iHct =  45.0% <- removal  of 1662 ml of fluids             to achieve Ideal Plasma Volume
                                AND removal  of 1133 ml of red cells          to achieve Ideal Red Cell Volume
-------------------------------------------------------------------------------------------------------
(moderately low)   vHct =  42.3% <- removal  of 2795 ml of whole blood        to achieve Ideal Blood Volume
(VERY LOW)         rHct =  34.0% <- removal  of 1133 ml of red cells          to achieve Ideal Red Cell Volume
(VERY HIGH)        aHct =  56.9% <- removal  of 1662 ml of fluids             to achieve Ideal Plasma Volume
(VERY HIGH)        fHct =  69.4% <- removal  of 2795 ml of fluids             to achieve Ideal Blood Volume
(VERY LOW)         tHct =   9.1% <- removal  of 2795 ml of red cells          to achieve Ideal Blood Volume
===============================================================================
```

FIG. 20

```
==================================================================================================
Patient 3259:(Female)

Blood Volume:     Current = 5338 ml | Ideal = 4213 ml | Deviation =  1125 ml = +26.7% (SEVERE EXCESS)
Plasma Volume:    Current = 3174 ml | Ideal = 2695 ml | Deviation =   479 ml = +17.8% (moderate excess)
Red Cell Volume:  Current = 2164 ml | Ideal = 1518 ml | Deviation =   646 ml = +42.6% (EXTREME EXCESS)

Status            Hct measure      Intervention                         Volume Target
--------------------------------------------------------------------------------------------------
(HIGH)            pHct = 45.0% <- CURRENT VALUE
(Ideal)           iHct = 40.0% <- removal  of  479 ml of fluids         to achieve Ideal Plasma Volume
                              AND removal  of  646 ml of red cells      to achieve Ideal Red Cell Volume
--------------------------------------------------------------------------------------------------
(moderately high) vHct = 43.7% <- removal  of 1125 ml of whole blood    to achieve Ideal Blood Volume
(LOW)             rHct = 35.9% <- removal  of  646 ml of red cells      to achieve Ideal Red Cell Volume
(VERY HIGH)       aHct = 49.4% <- removal  of  479 ml of fluids         to achieve Ideal Plasma Volume
(VERY LOW)        tHct = 27.4% <- removal  of 1125 ml of red cells      to achieve Ideal Blood Volume
(VERY HIGH)       fHct = 57.0% <- removal  of 1125 ml of fluids         to achieve Ideal Blood Volume
==================================================================================================

==================================================================================================
Patient 3907:(Female)

Blood Volume:     Current = 5836 ml | Ideal = 6048 ml | Deviation =  -212 ml =  -3.5% (normal deficit)
Plasma Volume:    Current = 3470 ml | Ideal = 3869 ml | Deviation =  -399 ml = -10.3% (mild deficit)
Red Cell Volume:  Current = 2366 ml | Ideal = 2179 ml | Deviation =   187 ml =  +8.6% (normal excess)

Status            Hct measure      Intervention                         Volume Target
--------------------------------------------------------------------------------------------------
(HIGH)            pHct  = 45.0% <- CURRENT VALUE
(Ideal)           iHct  = 40.0% <- addition of  399 ml of fluids        to achieve Ideal Plasma Volume
                               AND removal  of  187 ml of red cells     to achieve Ideal Red Cell Volume
--------------------------------------------------------------------------------------------------
(moderately high) aHct  = 42.1% <- addition of  399 ml of fluids        to achieve Ideal Plasma Volume
(moderately high) rHct  = 42.8% <- removal  of  187 ml of red cells     to achieve Ideal Red Cell Volume
(moderately high) fHct  = 43.4% <- addition of  212 ml of fluids        to achieve Ideal Blood Volume
(HIGH)            wiHct = 45.0% <- addition of  212 ml of whole blood (iHct) to achieve Ideal Blood Volume
(VERY HIGH)       w70Hct= 46.1% <- addition of  212 ml of packed red cells   to achieve Ideal Blood Volume
==================================================================================================
```

FIG. 21

```
===============================================================================
Patient 3513:(Female)

Blood Volume:      Current = 5288 ml | Ideal = 5067 ml | Deviation =   221 ml = +4.4% (normal excess)
Plasma Volume:     Current = 3144 ml | Ideal = 3241 ml | Deviation =   -97 ml = -3.0% (normal deficit)
Red Cell Volume:   Current = 2144 ml | Ideal = 1826 ml | Deviation =   318 ml = +17.4% (mild excess)

Status              Hct measure      Intervention                         Volume Target
-------------------------------------------------------------------------------------------------------
(HIGH)              pHct =  45.0% <- CURRENT VALUE
(Ideal)             iHct =  40.0% <- addition of   97 ml of fluids        to achieve Ideal Plasma Volume
                                 AND removal  of  318 ml of red cells     to achieve Ideal Red Cell Volume
(normal)            rHct =  40.8% <- removal  of  318 ml of red cells     to achieve Ideal Red Cell Volume
-------------------------------------------------------------------------------------------------------
(moderately high)   tHct =  42.1% <- removal  of  221 ml of red cells     to achieve Ideal Blood Volume
(HIGH)              aHct =  44.2% <- addition of   97 ml of fluids        to achieve Ideal Plasma Volume
(HIGH)              vHct =  44.8% <- removal  of  221 ml of whole blood   to achieve Ideal Blood Volume
(VERY HIGH)         fHct =  47.0% <- removal  of  221 ml of fluids        to achieve Ideal Blood Volume
===============================================================================
```

FIG. 22

BLOOD VOLUME ANALYSIS WITH VOLUME-AWARE BLOOD COMPONENT MEASURES AND TREATMENT

CROSS-REFERENCE TO RELATED APPLICATION

This application claims the benefit of U.S. Provisional Patent Application No. 62/451,813, filed on Jan. 30, 2017, the contents of which are herein incorporated by reference in their entirety into the present application.

FIELD OF THE INVENTION

The present invention relates to systems and methods for analyzing blood of a living being, and uses thereof.

BACKGROUND OF THE INVENTION

The Hematocrit (Hct) is a very widely-used and widely-available measure in medicine. It is generally defined as the percentage of packed cell by volume in a centrifuged sample of peripheral blood. Normal human values are considered to be 45% for males and 40% for females. Physicians are very familiar with this measurement, and many protocols and recommended treatments for a wide variety of medical conditions use thresholds and ranges of Hct values. However, in many medical situations, it is crucial to know the actual volume of a patient's blood, as well as the relative proportions of plasma and cells. As the measurement of patient blood volume is a somewhat more involved and less widely-available test, many physicians have become used to determining treatment based on Hct alone, even though understanding possible volume derangements would actually be very helpful.

The most direct result of a blood volume analysis is the report of the patient's volume status, with a comparison to ideal values. As volume irregularities have implications for a vast array of conditions, one intervention that is generally considered is correcting the irregularity, either directly or indirectly.

In the absence of a blood volume measurement, physicians have come to rely on surrogate measurements, even though these may be highly inaccurate proxies for an actual blood volume measurement. In particular, in considering whether a patient might require transfusion of blood components such red cells, plasma, or platelets, peripheral concentrations (e.g. Hct for red cells, platelet count for platelets) are used.

Consider the situation of acute blood loss, where transfusion might be contemplated. Surgeons and anesthesiologists, who are commonly involved in blood transfusion decisions, are usually aware of the shortcomings of proxies for blood volume; but they are often forced to rely on surrogate clinical findings such as arterial blood pressure, pulse rate, invasive procedures such as pulmonary arterial and central venous pressure, and occasionally wave form analysis when they are faced with a decision whether to administer or withhold transfusion. Physicians have often used peripheral Hct as a "trigger" for transfusion. In previous years, Hct guidelines such as 30% Hct was used as transfusion triggers; in recent years, transfusion triggers have been lowered to as low as 21% Hct even for patients in the 60-95 age range. These guidelines may be waived if clinical measurements such as hypotension indicate that a transfusion is necessary; one of the problems in the guidelines, particularly in acute situations, is that the homeostatic response to blood loss is the dilution of the remaining red blood cells by water into the intravascular blood space frequently takes many hours and may be incomplete because of confounding factors such as hypoalbuminemia. The process of compensation for blood loss is complex. The most basic immediate compensatory response to acute blood loss involves vasoconstriction resulting in decreased renal profusion, decreased blood flow to the skin and liver. At rest, the kidneys normally receive 25% of the cardiac output; of this blood flow, only approximately 4-5% is needed by the kidney for its metabolic needs; the kidney therefore as well as the other organs can tolerate significant reductions in blood flow without irreversible damage for limited time periods. The dilutive response of the remaining red blood cells therefore is a critical measurement with respect to whether to administer or withhold a transfusion. In a significant number of cases the change in peripheral blood pressure may occur very suddenly with a resultant catastrophic drop in blood pressure, which may lead to complications such as stroke, Myocardial infarction, renal failure, or death.

Volume considerations are also complex in non-acute blood loss situations. Chronic anemia is defined by low Hct levels and may be characterized by compensatory expansion of plasma volume. Such conditions are often complicated by confounding factors such as hypoalbuminemia. Hypoalbuminemia causes a fundamental change in the relationship of intravascular to interstitial water volume. In healthy individuals, intravascular volume is ⅓ of the interstitial volume; as hypoalbuminemia increases, to counterbalance the loss of osmotic pressure, the ratio of intravascular volume to interstitial volume will change so that a new ratio of 1:4, 1:6 or even greater may result. Under those conditions intravascular equilibrium will occur only in the presence of increased total body water and interstitial volume, as evidenced by increased peripheral edema; this is a common observation in post-operative conditions where patients are administered fluids to maintain systemic blood pressure.

Situations involving hypervolemia also confront practitioners with complex decisions. Polycythemia Vera may require therapeutic phlebotomy to reduce the risks associated with elevated Hct. Peripheral Hct typically underestimates the expansion of red cell volume which has taken place; such patients are at higher risk for stroke and heart attacks. Chronic heart failure as well as in certain pulmonary diseases is associated with increased red cell volume which may be masked by disproportionate increase in plasma volume. Phlebotomy may be performed in conjunction with diuretic used to reduce blood volume towards normal; excessive phlebotomy carries risk of stroke, heart attacks, and renal failure. Another treatment option for hypervolemia is ultrafiltration to remove excess fluid from the blood, while retaining blood proteins. Automated machines exist which can monitor the amount of fluid removed, as well as measure a reasonably accurate continuous peripheral Hct value. Knowledge of the patient's volemic status can be used to guide ultrafiltration treatment.

The present application and invention discloses a variety of metrics that can be derived from the measured Hct and other blood components when combined with the results of a Blood Volume Analysis that identifies the patient's Red Cell Volume, Plasma Volume, as well as normal values for those quantities. These derived metrics can then be used to guide treatment for a wide range of conditions. In a preferred embodiment of the present invention, an automated analyzer will help to guide and quantify treatment for volume derangements such as those discussed above. Serial blood volume measurements can be used to confirm successful adjustments, and/or indicate the need for further adjustments.

SUMMARY OF THE INVENTION

Systems and methods are presented for analyzing the blood of a living being. Equations are presented for volume-aware extension of the concept of Hematocrit, which are used for calculating volume-aware measures to evaluate and guide possible treatments. A system comprising an automated analyzer and a processor and other components is described which can carry out these calculations. According to one exemplary embodiment, the present invention comprises: an automated blood volume analyzer with a radiation counter, a sample changer, and a processor capable of calculating patient volumes, patient ideal volumes, and volume-aware Hematocrit measures. In one preferred embodiment, the analyzer provides a blood volume analysis report that includes volume-aware metrics, and also includes guidelines for indicated and contra-indicated treatments based on these metrics. Methods of diagnosis and treatment for volume abnormalities are described which are guided by the volume-aware Hct measures. In one exemplary embodiment, a method of diagnosis and treatment for plasma volume excess using ultrafiltration is described. In another exemplary embodiment, a method of diagnosis and treatment for red cell volume excess using erythrocytapheresis is described. In another exemplary embodiment, a method of diagnosis and treatment for conditions requiring transfusions of blood components such as plasma and red cells is presented, where the euvolemic concentrations of hemoglobin and albumin are used to guide treatment.

BRIEF SUMMARY OF EMBODIMENTS OF THE PRESENT INVENTION

The following presents a set of equations that can be used to derive volume-aware Hct metrics, as part of a system or method for analyzing patient blood. These metrics might be presented to the physician by themselves, or as adjunct to the results of a Blood Volume analysis. In one preferred embodiment, the equations are integrated into the software of an automated Blood Volume Analyzer such as described in U.S. Pat. No. 5,024,231, incorporated herein by reference, and the metrics are reported along with the rest of the Blood Volume Analysis report. In another preferred embodiment, the automated analyzer uses a light-based tracer (dye or fluorescent) rather than a radioactive tracer such as I-131. In another preferred embodiment, the equations are used to determine a method of treatment for volume abnormalities.

BRIEF DESCRIPTION OF THE DRAWINGS

The drawings, which are incorporated herein, illustrate one or more embodiments of the present invention, thus helping to better explain one or more aspects of the one or more embodiments. As such, the drawings are not to be construed as limiting any particular aspect of any embodiment of the invention. In the drawings:

FIG. 9 shows a sample report, reporting values of volume-aware Hematocrit measures.

FIG. 10 shows a sample Blood Volume Analysis report, incorporating reporting values of volume-aware Hematocrit measures.

FIG. 11 shows a table of example Volemic States, with notes regarding the application of volume-aware Hematocrit measures.

FIG. 12 shows a sample definition of descriptive ranges for Hct measures.

FIG. 13 and FIG. 14 each show a table of patient data with blood volume and Hct measures, with highlighting indicating normal and near-normal Hct measures. Different patients are reported in FIG. 13 and FIG. 14.

FIG. 15 shows a table relating Hct measures to treatment types.

FIG. 16-FIG. 22 each show sample Hct correction reports for exemplary patient cases. Different patients are reported in FIG. 16-FIG. 22.

DETAILED DESCRIPTION OF THE INVENTION

Figure 1:
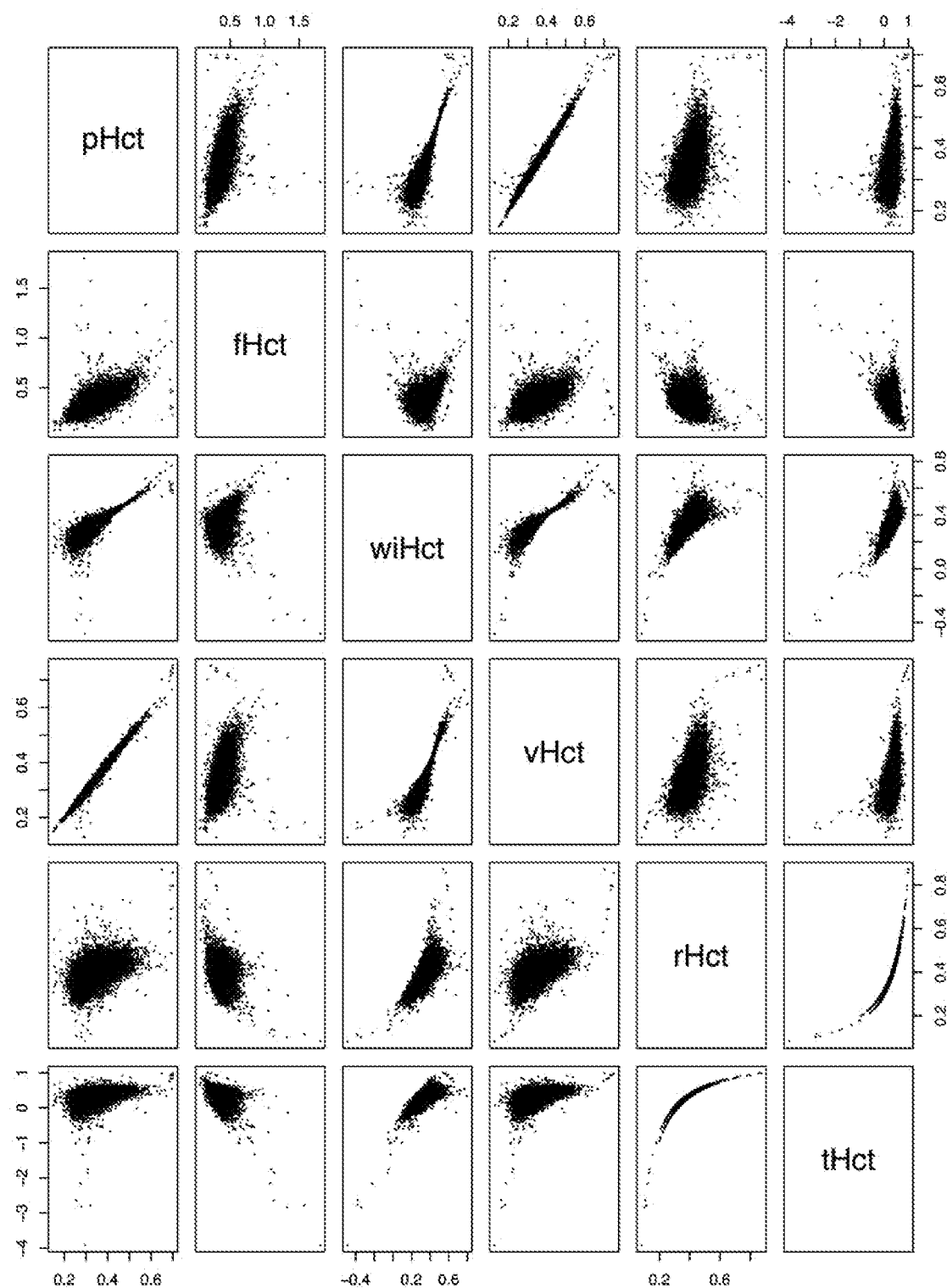
FIG. 1 shows a set of scatter plots that depict the relationships between peripheral Hct (pHct) and five other volume-aware Hct metrics defined herein. Each dot represents a single case taken from a database of over 14,000 blood volume measurements

It is assumed that a Blood Volume Analysis is available for a patient, including values for the following quantities: Blood Volume (BV), Plasma Volume (PV), Red Cell Volume (RCV), and that normal values are also derived from knowledge of the patient's gender, height and weight: Ideal Blood Volume (iBV), Ideal Plasma Volume (iPV) and Ideal Red Cell Volume (iRCV). Such values can be derived by consulting the relationship described in "Prediction of the Normal Blood Volume" (Feldschuh et al, Circulation, vol. 56, No. 4, October 1977, pp. 605 612.). In a preferred embodiment, all these values are taken from an automated Blood Volume Analyzer such as described in U.S. Pat. No. 5,024,231. This analyzer use radio-labeled I-131. The contents of that patent are herein incorporated by reference. It is also assumed that a peripheral Hct (pHct) is available.

The overall whole body Hct (oHct) is related to the peripheral Hct by the following relationship:

$$oHct = pHct * paf \qquad (1)$$

where $$paf = 0.9009 \qquad (2).$$

This is due to the fact that blood cells are more concentrated in the peripheral circulation (from which blood samples are drawn) than the average value for the whole body; the constant paf is derived as the product 0.99*0.91, as described in U.S. Pat. No. 5,024,231, or a similar constant value. Red Cell Volume and Plasma volume are related to Blood Volume as follows:

$$BV = PV + RCV \quad (3)$$

$$RCV = BV * oHct = BV * pHct * paf \quad (4)$$

$$PV = BV * (1 - oHct) = BV * (1 - pHct * paf) \quad (5).$$

The Ideal Hct (iHct) is defined to be:

$$iHct \equiv \begin{cases} 0.45 & \text{for Males} \\ 0.40 & \text{for Females} \end{cases} \quad (6)$$

The Ideal Red Cell Volume (iRCV) and Ideal Plasma Volume (iPV) are calculated from the iBV. Note that the iHct is a peripheral Hct value, so the peripheral adjustment factor is required:

$$iBV = iPV + iRCV \quad (7)$$

$$iRCV = iBV * iHct * paf \quad (8)$$

$$iPV = iBV - iRCV = iBV * (1 - iHct * paf) \quad (9).$$

Define the abbreviation "dev" to mean the deviation of a measured value from its respective Ideal value:

$$devBV = BV - iBV \quad (10)$$

$$devRCV = RCV - iRCV \quad (11)$$

$$devPV = PV - iPV \quad (12).$$

Define the abbreviation "edr" to mean the excess-deficit ratio of the deviation of a measured value from its Ideal value:

$$edrBV = \frac{devBV}{iBV} \quad (13)$$

$$edrRCV = \frac{devRCV}{iRCV} \quad (14)$$

$$edrPV = \frac{devPV}{iPV}. \quad (15)$$

Volume-aware metrics can now be defined that incorporate actual and ideal volume measurements into a single ratio-like (i.e. unit-less) value.

The fluid corrected Hematocrit (fHct) is defined to be the peripheral Hct that would be observed, if the patient's plasma volume were adjusted so that the patient's blood volume is the Ideal Blood Volume:

$$fHct = \left(\frac{RCV}{iBV}\right) \bigg/ paf. \quad (16)$$

Note that with reference to the above equation defining RCV, the fHct can also be expressed in terms of the pHct, removing the paf factor:

$$fHct = pHct * \frac{BV}{iBV}. \quad (17)$$

It is also possible, with reference to Equation (8) defining iRCV, to express fHct in terms of the ratio of the Red Cell Volume to the Ideal Red Cell Volume:

$$fHct = iHct * \frac{RCV}{iRCV} = iHct * (1 + edrRCV). \quad (18)$$

The clinical analog of the fHct is a potential removal of fluids (e.g. by diuresis or plasmapheresis/ultrafiltration) or addition of fluids (e.g. by transfusion of plasma or other fluids). A potential interpretation of the fHct is to assess whether such a procedure would leave the patient with an acceptable Hct. For example, hypervolemic patients often exhibit low pHct. The fHct is useful for distinguishing between dilutional (apparent) anemia which does not indicate a compromised oxygen transport capability, and true anemia. As a concrete example, consider two hypervolemic female patients with a pHct of 20. Patient A has a Blood Volume that is 100% expanded: BV=2iBV. This patient has fHct=0.40, so her anemia is purely dilution. Patient B has a blood volume that is only 20% expanded (BV=1.2iBV), so her fHct=24, which suggests a dangerous level of true anemia.

Note that fHct can be greater than 1 in situations of extreme hypervolemia (if RCV>iBV*paf), indicating that it is not possible to achieve the ideal Blood Volume solely by removing fluid.

A related measure is the plasma volume corrected Hct (aHct), which is defined to be the peripheral Hct that would be observed if the patient's plasma volume were adjusted so that the patient's Plasma Volume is the Ideal Plasma Volume:

$$aHct = \left(\frac{RCV}{RCV + iPV}\right) \bigg/ paf. \quad (19)$$

The whole blood corrected Hematocrit ($w_b$Hct) is defined to be the peripheral Hct that would be observed if the patient were given (or had removed) whole blood with a red cell to plasma ratio of bHct, so that the patient's blood volume is the Ideal Blood Volume:

$$w_b Hct = \left(\frac{RCV + bHct * (iBV - BV)}{iBV}\right) \bigg/ paf. \quad (20)$$

Several particular values for bHct have clinical interest. If BV<iBV, then a transfusion of whole blood or its equivalent might be considered, using the ideal Hct value, so the whole blood ideal corrected Hematocrit ($w_i$Hct) is defined:

$$w_i Hct = \left(\frac{RCV + iHct * (iBV - BV)}{iBV}\right) \bigg/ paf. \quad (21)$$

Another value of clinical interest for bHct is 70%, the typical concentration of red cells in prepared units of red cells for transfusion. In this case, the whole blood corrected Hct obtained when correcting the patient's total blood volume using packed red cells ($w_{70}$Hct) is of interest in evaluating transfusion treatment, typically when BV<IBV:

$$w_{70}Hct = \left(\frac{RCV + 0.7*(iBV - BV)}{iBV}\right)/paf. \quad (22)$$

If BV>iBV, then a venesection (removal of whole blood) might be considered. Then bHct=pHct, so the following venesection corrected Hct (vHct) is defined:

$$vHct = w_p Hct = \left(\frac{RCV - pHct*(BV - iBV)}{iBV}\right)/paf. \quad (23)$$

Substituting for RCV and simplifying, $$vHct = \left(\frac{pHct*BV*paf + pHct*(iBV - BV)}{iBV}\right)/paf \quad (24)$$

$$vHct = pHct*\left(\frac{iBV - BV(1 - paf)}{iBV}\right)/paf \quad (25)$$

$$vHct = pHct*\left(\frac{1 - (1 - paf)*\frac{BV}{iBV}}{paf}\right). \quad (26)$$

Note that this last equation implies that vHct approaches pHct as BV approaches iBV. This equation captures the idea that the final observed peripheral Hct will decrease with venesection, as the peripheral blood being removed is more concentrated than the entire blood supply. This equation does not attempt to capture dynamic effects that may arise as the actual peripheral Hct is reduced during the process of venesection. A slower venesection will likely produce more compensation than a fast one. The following relation holds due to these dynamic compensation effects for the final venesection corrected peripheral Hct ($v_f$Hct):

$$\begin{cases} vHct \leq v_f Hct \leq pHct & \text{when } BV > iBV \\ pHct \leq v_f Hct \leq vHct & \text{when } BV < iBV \end{cases} \quad (27)$$

The final venesection corrected peripheral Hct range is hence defined as [vHct, pHct]. Note that although Equation (27) states the relation for the second case when BV<iBV, this is not readily interpretable as a venesection correction as in this case the patient is not hypervolemic but rather hypovolemic.

The red cell volume corrected Hematocrit (rHct) is defined to be the peripheral Hct that would be observed if the patient had removed (e.g. by erythrocytapheresis) red blood cells so that the patient's red blood cell volume is the Ideal Red Blood Cell Volume:

$$rHct = \left(\frac{iRCV}{BV + (iRCV - RCV)}\right)/paf \quad (28)$$
$$= \left(\frac{iRCV}{BV - devRCV}\right)/paf$$

Note that the denominator is guaranteed to be positive, since BV>RCV. This can be expressed in terms of PV as:

$$rHct = \left(\frac{iRCV}{iRCV + PV}\right)/paf. \quad (29)$$

When red cell addition is contemplated, the measure packed red cell volume corrected Hematocrit ($r_{70}$Hct) is defined to be the peripheral Hct that would be observed if the patient were given (e.g. by red blood cell transfusion) red blood cells so that the patient's red blood cell volume is the Ideal Red Blood Cell Volume, taking into account the typical 70% Hct of packed red cells:

$$r_{70}Hct = \left(\frac{iRCV}{BV + (iRCV - RCV)/0.7}\right)/paf. \quad (30)$$

The red cell total blood volume corrected Hematocrit (tHct) is defined to be the peripheral Hct that would be observed, if the patient had removed (e.g. by Erythrocytapheresis) red blood cells so that the patient's total blood cell volume is the Ideal Blood Volume:

$$tHct = \left(\frac{RCV + (iBV - BV)}{iBV}\right)/paf. \quad (31)$$
$$= \left(\frac{RCV - devBV}{iBV}\right)/paf$$

This can be simplified as:

$$tHct = \left(1 - \frac{PV}{iBV}\right)/paf. \quad (32)$$

Note that although tHct is reasonably bounded for low values of PV, tHct is not guaranteed to be positive for high values of PV. The clinical interpretation of this is as follows: For hypovolemia, devBV is negative; a tHct above a certain level would indicate that restoring Ideal blood volume only with red cells would not be advisable and plasma should be given as well; for hypervolumia, devBV is positive, and a low tHct would indicate that correcting Total Blood Volume derangement by removing red blood cells only would be inadvisable, and a negative tHct would indicate that such a correction would be impossible, because devBV>RCV.

Note that the ratio of tHct and rHct can be expressed solely in terms of the ratio PV/iBV and iHct:

$$\frac{tHct}{rHct} = \left(1 - \frac{PV}{iBV}\right)/\left(\frac{1}{1 + \frac{PV}{iRCV}}\right) \quad (33)$$
$$= \left(1 - \frac{PV}{iBV}\right)*\left(1 + \left(\frac{1}{iHct*paf}\right)\frac{PV}{iBV}\right)$$

Comparison of the defining equations also shows that:

$$tHct = w_{100}Hct \quad (34).$$

As pHct is a measurement that can be performed quickly and easily (and in fact can be monitored continuously in many cases), the various corrected hematocrits disclosed above can be used as target values to guide safer and more effective treatment that insures that the patient's volemic status will be close to normal at the end of treatment, and avoids the considerable risks associated with possible under-treatment or over-treatment. Consider, for example, the case of ultrafiltration (apheresis) to treat hypervolemia due to congestive heart failure. Such patients will have a low pHct before treatment, but without knowledge of the patient's blood volume status it is unclear how much the pHct is lowered due to dilutional anemia (i.e. excess plasma volume) and how much due to true anemia (i.e. low red cell volume). Using the iHct as a target value for ultrafiltration treatment is potentially very dangerous for a patient with true anemia, as it could result in a dangerous loss of blood pressure and related complications due to low blood volume. Using the fHct as a target value for ultrafiltration insures that the patient will have normal blood volume at the conclusion of the ultrafiltration procedure.

It is also possible and desirable to consider the effect on other measured concentrations besides Hct (which can be thought of as the concentration of red blood cells in whole blood). Consider an arbitrary quantity X which is expressed in units/volume of blood. The patient's total vascular supply of X is then X*BV. A preserving correction procedure for X is defined as an actual or proposed treatment or intervention that 1) adjusts the patient's blood volume to be the ideal (euvolumic) blood volume, and that also 2) does not add or remove X from the bloodstream. For example, the fluid corrected Hct (fHct) procedure satisfies conditions 1 and 2 for the concentration of red blood cells in whole blood. Following such a correction procedure, the euvolemic concentration of X (eX) that will be observed is changed by the ratio of V/iV, where V is the volume component that this being considered for purposes of concentration, and iV is the volume for that component after a correction to the ideal has been made:

$$eX = X * \frac{V}{iV}. \tag{35}$$

The euvolemic concentration correction factor is defined:

$$\text{euvolemic concentration correction factor} \equiv \frac{V}{iV}. \tag{36}$$

Some concentrations (e.g. hemoglobin, discussed below) are quoted in terms of whole blood volume, so:

$$\text{euvolemic whole blood concentration correction factor} = \frac{BV}{iBV} \tag{37}$$

Other concentrations (e.g. albumin, discussed below) are defined in terms of plasma volume, so:

$$\text{euvolemic plasma concentration correction factor} = \tag{38}$$

$$\frac{PV}{PV + (iBV - BV)}.$$

Note that the denominator in equation (38) is not iPV, but rather the plasma volume that results from correcting BV to iBV using fluids.

In a preferred embodiment, an automated analyzer displays the euvolemic concentration correction factors for use in adjusting any measurements of interest that satisfy the preserving correction procedure conditions.

For example, albumin is a crucial blood component. It is a high molecular weight protein (66 kDa) that is responsible for maintaining oncotic pressure in the circulation. Ultrafiltration is a fluid-removal procedure that preserves albumin in the bloodstream (as albumin is too large to pass through the membranes used), so ultrafiltration is a preserving correction procedure for albumin, and a euvolemic Albumin concentration can be defined:

$$eAlbumin = \text{Albumin} * \frac{PV}{PV + (iBV - BV)} \tag{39}$$

Note that the euvolemic plasma concentration correction factor is used, as albumin concentration is quoted as a serum concentration. In contrast, plasmapheresis using techniques such as centrifugation (in which red blood cells are separated and returned, and albumin-containing plasma is removed) is not a preserving correction procedure for albumin, and the above equation does not apply.

Another important example is Hemoglobin concentration (Hb). This is a measurement that is generally available as part of a complete blood count (CBC) test, and measures the concentration of the blood protein that makes up the bulk of the dry weight red blood cells and that performs the oxygen transport function of these cells. Research has shown (e.g. "MYTH OR REALITY: HEMATOCRIT AND HEMOGLOBIN DIFFER IN TRAUMA", Niljboer et al., *J Trauma* 2007; 62(5):1310-2) that Hct and Hb are very highly correlated, particularly in urgent-care situations. Many current transfusion guidelines (e.g. "Clinical Practice Guidelines From the AABB: Red Blood Cell Transfusion Thresholds and Storage", *JAMA*. 2016; 316(19):2025 2035. doi: 10.1001/jama.2016.9185) refer to Hb levels as decision trigger points, despite uncertainty as to how a patient's volemic status may have distorted the observed Hb. To this end, it is helpful to display a euvolemic Hemoglobin concentration:

$$eHb = Hb * \frac{BV}{iBV}. \tag{40}$$

Such a euvolemic Hemoglobin concentration can be used in place of the uncorrected value in transfusion guidelines. Note that the euvolemic whole blood concentration correction factor is used, as Hemoglobin concentration is quoted as a whole blood concentration.

In another preferred embodiment, an automated analyzer displays euvolemic concentration values for a plurality of measurements of interest, such as those contained in a CBC test, using the actual measured concentration values of said measurements, and compares the euvolemic values to reference values, producing a report. These measurements are entered into the processor via manual input, or by accessing a patient's medical record through a connection to a database. In another preferred embodiment, a method of treatment and diagnosis uses such euvolemic concentration values in place of uncorrected values.

Another preferred embodiment provides a system for automatically analyzing blood of a human subject comprising a concentration counter configured to analyze one or more samples, a user interface operatively connected to the concentration counter and configured for entry and display of information, one or more processors operatively coupled to a memory and configured to execute programmed instructions stored in the memory to carry out a method comprising the steps of:

a. gathering data related to the concentration of a tracer (such as a radioactive isotope, or a fluorescent dye) within samples of blood from a human patient;

b. calculating, by the one or more processors, a blood volume (BV), plasma volume (PV), and red cell volume (RCV) for the patient;

c. calculating, by the one or more processors, an ideal blood volume (iBV), ideal plasma volume (iPV), and red cell volume (iRCV) for the patient based on patient descriptive data such as height, weight, and gender;

d. calculating, by the one or more processors, a fluid corrected Hct (fHct) defined to be the peripheral Hct that would be observed, if the patient's plasma volume were adjusted so that the patient's blood volume is the Ideal Blood Volume $$\left(\text{e.g., } fHct = \left(\frac{RCV}{iBV}\right) \middle/ paf\right),$$

where the peripheral adjustment factor paf is a constant value (0.9009));

e. calculating one or more of the following values:

i. plasma volume corrected Hct (aHct), which is defined to be the peripheral Hct that would be observed if the patient's plasma volume were adjusted so that the patient's Plasma Volume is the Ideal Plasma Volume $$\left(\text{e.g., } aHct = \left(\frac{RCV}{RCV + iPV}\right) \middle/ paf\right);$$

ii. whole blood corrected Hematocrit ($w_b$Hct), which is defined to be the peripheral Hct that would be observed if the patient were given (or had removed) whole blood with a red cell to plasma ratio of bHct, so that the patient's blood volume is the Ideal Blood Volume $$\left(\text{e.g., } w_b Hct = \left(\frac{RCV + bHct*(iBV - BV)}{iBV}\right) \middle/ paf\right);$$

iii. whole blood ideal corrected Hematocrit ($w_i$Hct), which is defined as the whole blood corrected Hematocrit ($w_b$Hct) where bHct is the ideal Hct for the patient (e.g., using the ideal Hct value iHct (40% for women, 45% for men):

$$w_i Hct = \left(\frac{RCV + iHct*(iBV - BV)}{iBV}\right) \middle/ paf;$$

iv. whole blood corrected Hct obtained when correcting the patient's total blood volume using packed red cells ($w_{70}$Hct)

$$\left(\text{e.g., } w_{70} Hct = \left(\frac{RCV + 0.7*(iBV - BV)}{iBV}\right) \middle/ paf\right);$$

v. venesection corrected Hct (vHct), defined to be the peripheral Hct that would be observed if the patient had blood removed (with the patient's observed peripheral Hct (pHct)) to achieve Ideal Blood Volume $$\left(\text{e.g., } vHct = \left(\frac{RCV - pHct*(BV - iBV)}{iBV}\right) \middle/ paf\right),$$

together with a final venesection corrected peripheral Hct range defined to be the peripheral Hct that would be observed after a venesection was performed over a time period allowing for fluid compensation, calculated as [vHct, pHct];

vi. red cell volume corrected Hematocrit (rHct), defined to be the peripheral Hct that would be observed if the patient had removed (e.g. by erythrocytapheresis) red blood cells so that the patient's red blood cell volume is the Ideal Red Blood Cell Volume $$\left(\text{e.g., } rHct = \left(\frac{iRCV}{BV + (iRCV - RCV)}\right) \middle/ paf\right);$$

vii. packed red cell volume corrected Hematocrit ($r_{70}$Hct), defined to be the peripheral Hct that would be observed if the patient were given (e.g. by red blood cell transfusion) red blood cells so that the patient's red blood cell volume is the Ideal Red Blood Cell Volume, taking into account the typical 70% Hct of packed red cells $$\left(\text{e.g., } r_{70} Hct = \left(\frac{iRCV}{BV + (iRCV - RCV)/0.7}\right) \middle/ paf\right);$$

and viii. red cell total blood volume corrected Hematocrit (tHct), defined to be the peripheral Hct that would be observed, if the patient had removed (e.g. by erythrocytapheresis) red blood cells so that the patient's total blood cell volume is the Ideal Blood Volume $$\left(\text{e.g., } tHct = \left(\frac{RCV + (iBV - BV)}{iBV}\right) \middle/ paf\right);$$

and f. displaying, by the one or more processors, at the user interface, one or more of the values calculated in step (e) so as to provide an analysis of the samples of blood; thereby analyzing the subject's blood.

The step of gathering data related to the concentration of a tracer within samples of blood from a human patient can comprise injecting a tracer into the bloodstream of the human subject, collecting blood samples from the human subject over a time period after injection; and measuring the concentration of the tracer in the various samples. In one embodiment, the tracer can be a radioactive isotope, and the counter is a radiation counter equipped with one or more counting wells, with or without a mechanism for moving samples into counting wells. In another embodiment, the tracer can be a light-emitting (fluorescent) or light-absorbent (dye), and the counter is capable of measuring light emission or absorption either in multiple samples conveyed to the counter, or by direct measurement of circulating patient blood.

Euvolemic concentration correction factors can be calculated for whole blood and/or plasma. For example, one or more of the following can be calculated: euvolemic Hemoglobin concentration, and/or euvolemic Albumin concentration. In one embodiment, a plurality of patient concentrations (such as generated by a CBC test) are entered into the processor (via manual input, or through access to a database or medical record) and a report is generated comparing the euvolemic values for each concentration (calculated using the relevant euvolemic concentration correction factor) to the standard reference ranges for each concentration.

In a preferred embodiment, such an analyzer also prepares a report that uses these corrected Hct value to diagnose and guide treatment by comparing corrected Hct values to reference ranges. Such a report can guide treatment by explicit instructions, by emphasizing certain treatments through various means of presentation (by use of formatting and ordering of information), and by quoting related treatment guidelines (for example from established medical panels).

A report of the subject's condition can be generated listing the corrected Hct values for a patient, along with a normal range. The report can be generated listing and quantifying the interventions associated with each corrected Hct value. The report can include descriptive text based on reference ranges associated with each intervention. The interventions can be listed in order of suitability, defined by distance of relevant Hct measure from iHct. The formatting of the report (lines, colors, highlighting, size, etc.) can be used to distinguish interventions that are close to normal, or far away from normal. One or more of the corrected measures can be used as a target value for an intervention aimed at establishing an ideal volume for a patient. For example, the intervention can be ultrafiltration, and the target value is some function of aHct, fHct, and iHct. As another example, the intervention can be erythrocytapheresis, and the target value is some function of rHct, tHct, and iHct. A continuous, real-time measurement of Hct can incorporated into the system to automatically terminate the intervention when the target is reached.

In another embodiment, such an analyzer quotes a target value for Hct to be used in the course of a volume-adjusting treatment (such as ultrafiltration or erythrocytapheresis). In a preferred embodiment, the analyzer is connected to a device performing such a treatment and to a real-time Hct measurement, and is capable of controlling the treatment (e.g. by automatically stopping it, or by alerting the operator) in response to changes in Hct. In a preferred embodiment, some function/combination of aHct, fHct, and iHct is used as the target for ultrafiltration; such a function might be the mean, the min, the max, the first reached, or simply one of the values, etc. In a preferred embodiment, some function/combination of rHct, tHct, and iHct is used as the target for erythrocytapheresis.

In another embodiment, a BVA analyzer reports euvolemic corrections for blood test values such as from a CBC report (which may be entered manually into the BVA analyzer, or via electronic connection).

The invention also provides a method of treating a patient for a blood, plasma, or red-cell volume abnormality, comprising: analyzing the blood of the patient with any of the systems for automatically analyzing blood of a subject disclosed herein to obtain a corrected Hct value and thereby identify a blood, plasma, or red-cell volume abnormality; and selecting an appropriate treatment for the abnormality and administering the treatment to the patient. The treatment, for example, can be ultrafiltration, where ultrafiltration is continued until a target Hct is reached, the target value being determined as a function of fHct, aHct, and/or iHct. Tin another example, the treatment can be erythrocytapheresis, where erythrocytapheresis is continued until a target Hct is reached, the target value being determined as a function of fHct, aHct, and/or iHct.

Also provided is a method of treating a patient for a blood, plasma, or red-cell volume abnormality, comprising administering an appropriate treatment for the abnormality to the patient, wherein the abnormality has previously been identified by analyzing a blood sample of the patient with any of the systems for automatically analyzing blood of a subject disclosed herein to obtain a corrected Hct value and thereby identify a blood, plasma, or red-cell volume abnormality, where, e.g., the treatment is ultrafiltration or erythrocytapheresis.

In addition to human subjects, the invention can also be used with other mammals, such as veterinary patients, livestock, or zoo animals.

FIG. 1 shows a set of scatter plots that depict the relationships between peripheral Hct (pHct) and five other volume-aware Hct metrics defined above. Each scatter plot dot represents a single case, taken from a database of 14,747 cases performed over a number of years at five different hospitals. They illustrate the relationship between the various measures. One immediately striking aspect of the figure is that there is a large amount of heterogeneity—a given pHct value can result in a wide range of values for the other measures. This is evidenced by the fact that the points spread out into broad clouds—in other words, the volume state determined by the blood volume measurement has a large amount of variance, which translates into variance of the other measures.

Figure 2:
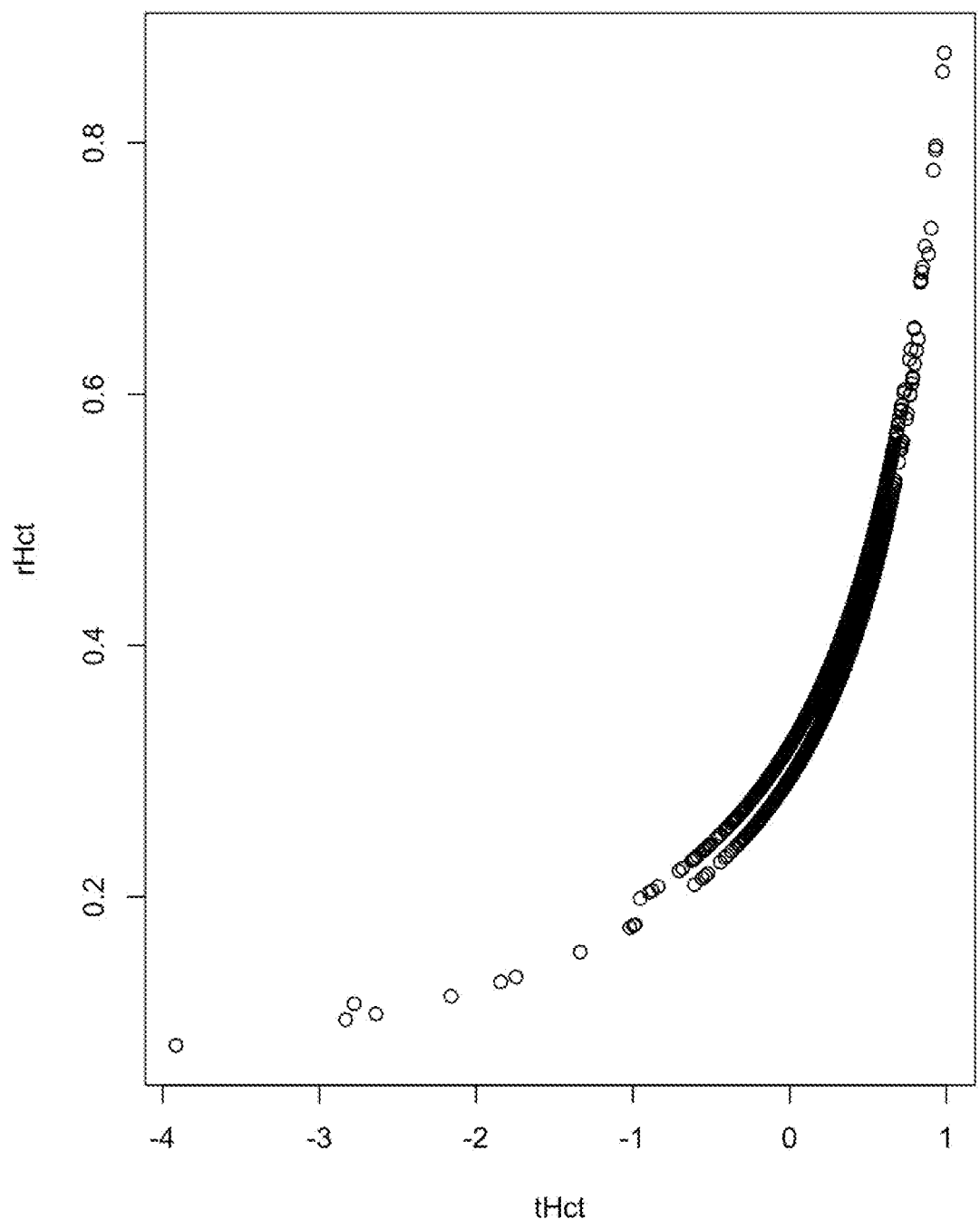
FIG. 2 shows a detail of one of the panels from FIG. 1, showing the relationship between red cell total blood volume corrected Hematocrit (tHct) and red cell volume corrected Hematocrit (rHct).

A few exceptions to this can be seen, and are understandable with reference to the defining equations above. The two-part curvilinear relationship between tHct and rHct seen in FIG. 2 is explained by equation (33): iHct depends only on gender; for each gender, tHct/rHct will trace a segment of the parabola defined by the equation:

$$y=(1-x)*(1+kx) \qquad (41)$$

where $k=1/(iHct*paf)$, and x takes on values in the range (min(PV/iBV), max(PV/iBV)). For the database of cases depicted in FIG. 1 this range is (0.11, 4.53), with the inter-quartile range being (0.60, 0.79).

Figure 3:
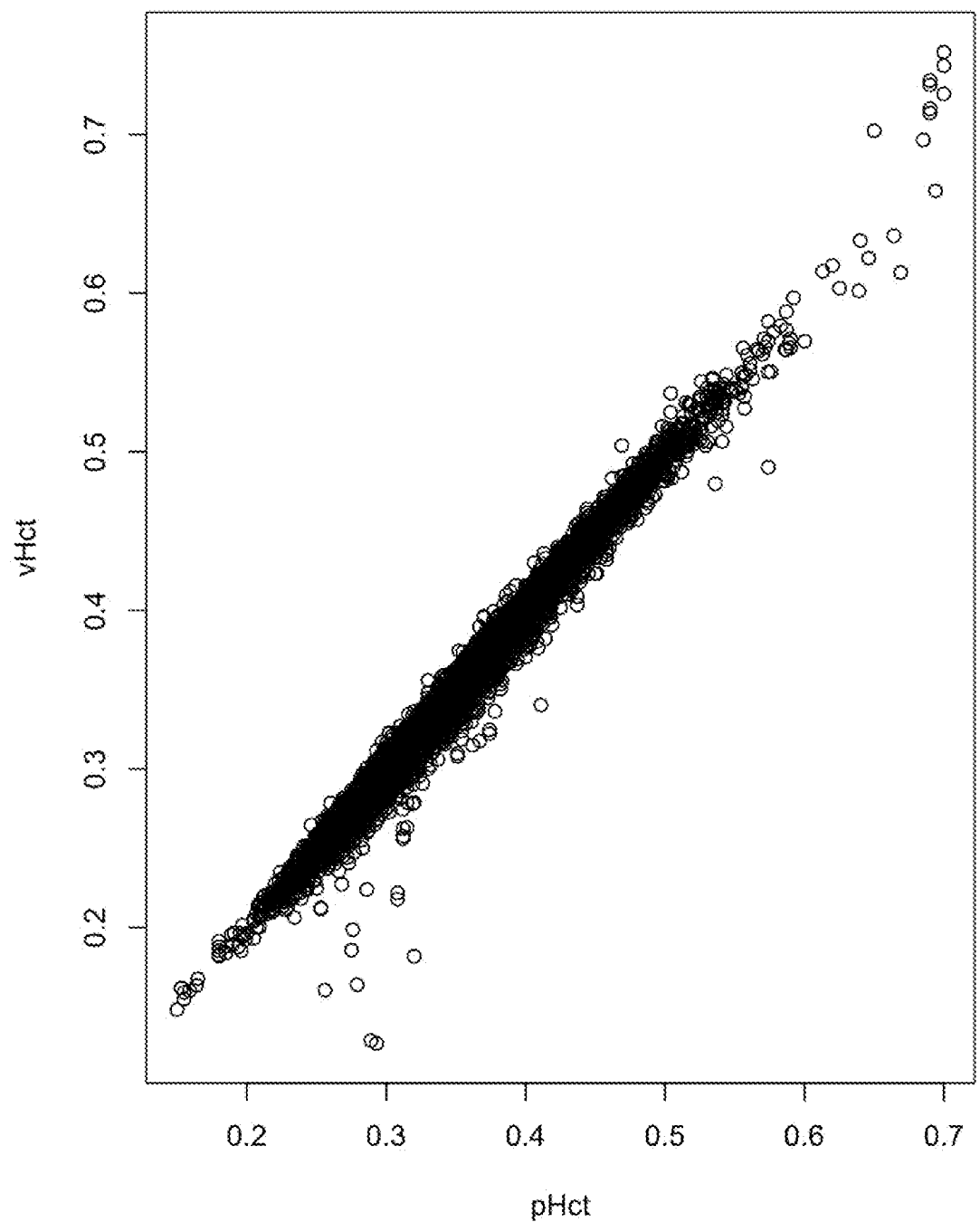
FIG. 3 shows a detail of one of the panels from FIG. 1, showing the relationship between pHct and venesection corrected Hct (vHct).

The relationship between pHct and vHct, shown in FIG. 3, is clustered around a line of equality. Consulting Equations (26) and (2), the ratio vHct/pHct can be expressed as:

$$\frac{vHct}{pHct} = 1.11 - 0.11 * \frac{BV}{iBV}. \qquad (42)$$

Figure 4:
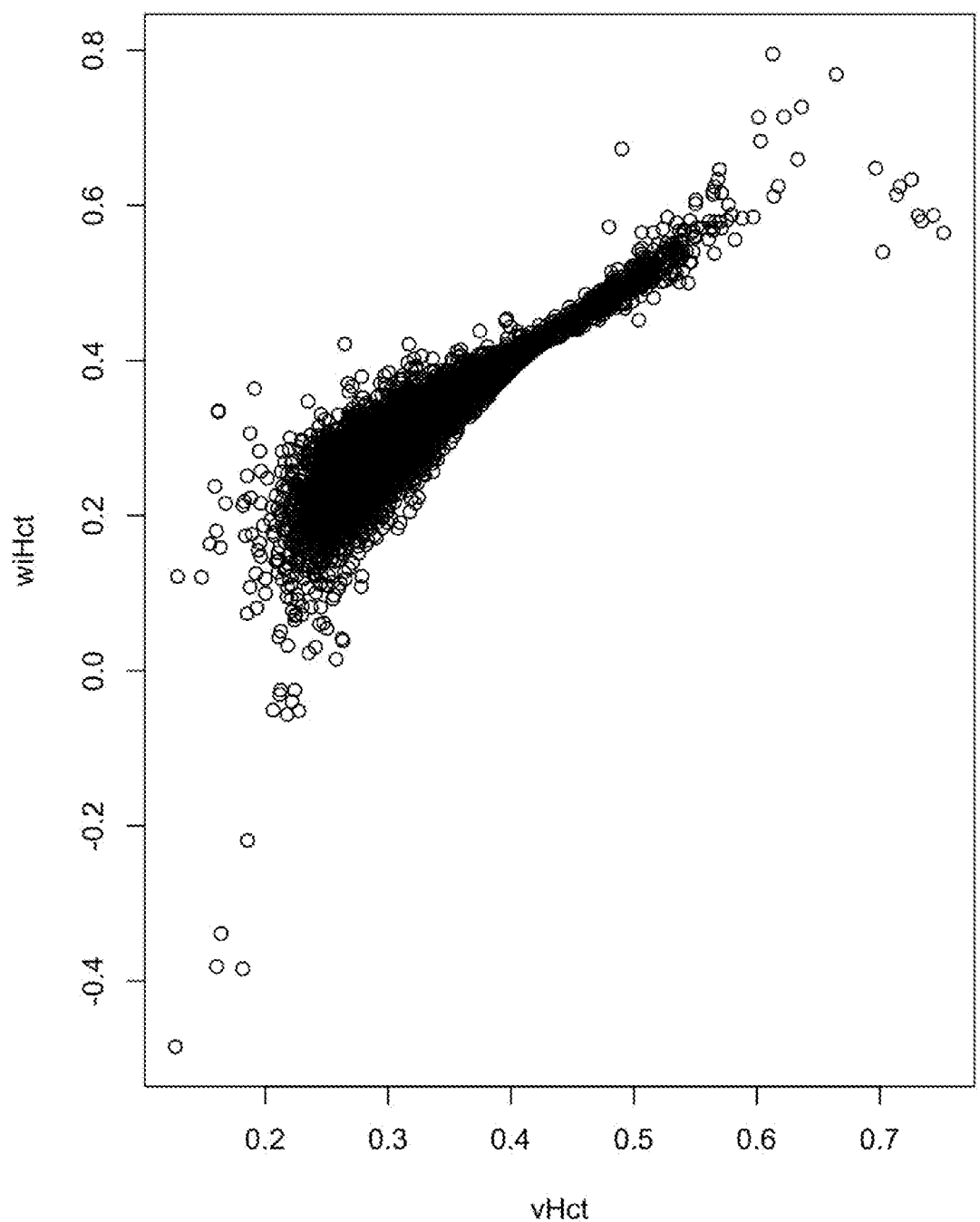
FIG. 4 shows a detail of one of the panels from FIG. 1, showing the relationship between vHct and whole blood ideal corrected Hematocrit (wiHct).

The relationship between $w_rHct$ and both vHct, shown in FIG. 4, has an interesting dumbbell shape, marked by close agreement in the region where vHct is close to iHct, and divergence when vHct is significantly greater or smaller than iHct. This relationship can be understood by examining Equation (23), which defines vHct as a special case of $w_bHct$. The close relationship of vHct and pHct as discussed above results in a similar dumbbell shape for the scatter plot of $w_rHct$ with pHct.

Figure 5:
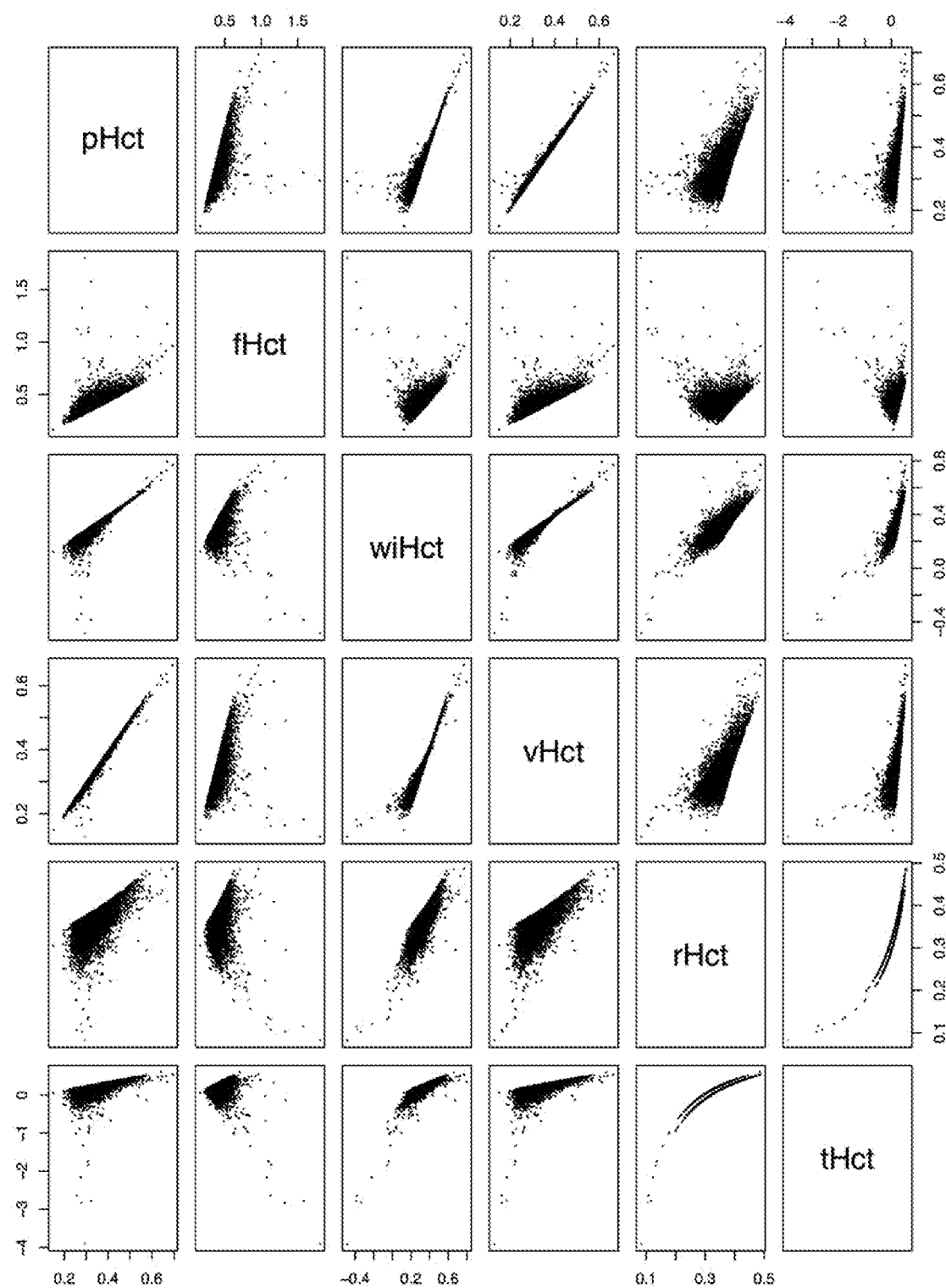
FIG. 5 shows a similar set of scatter plots as in FIG. 1, showing only cases where hypervolemia was present.
Figure 6:
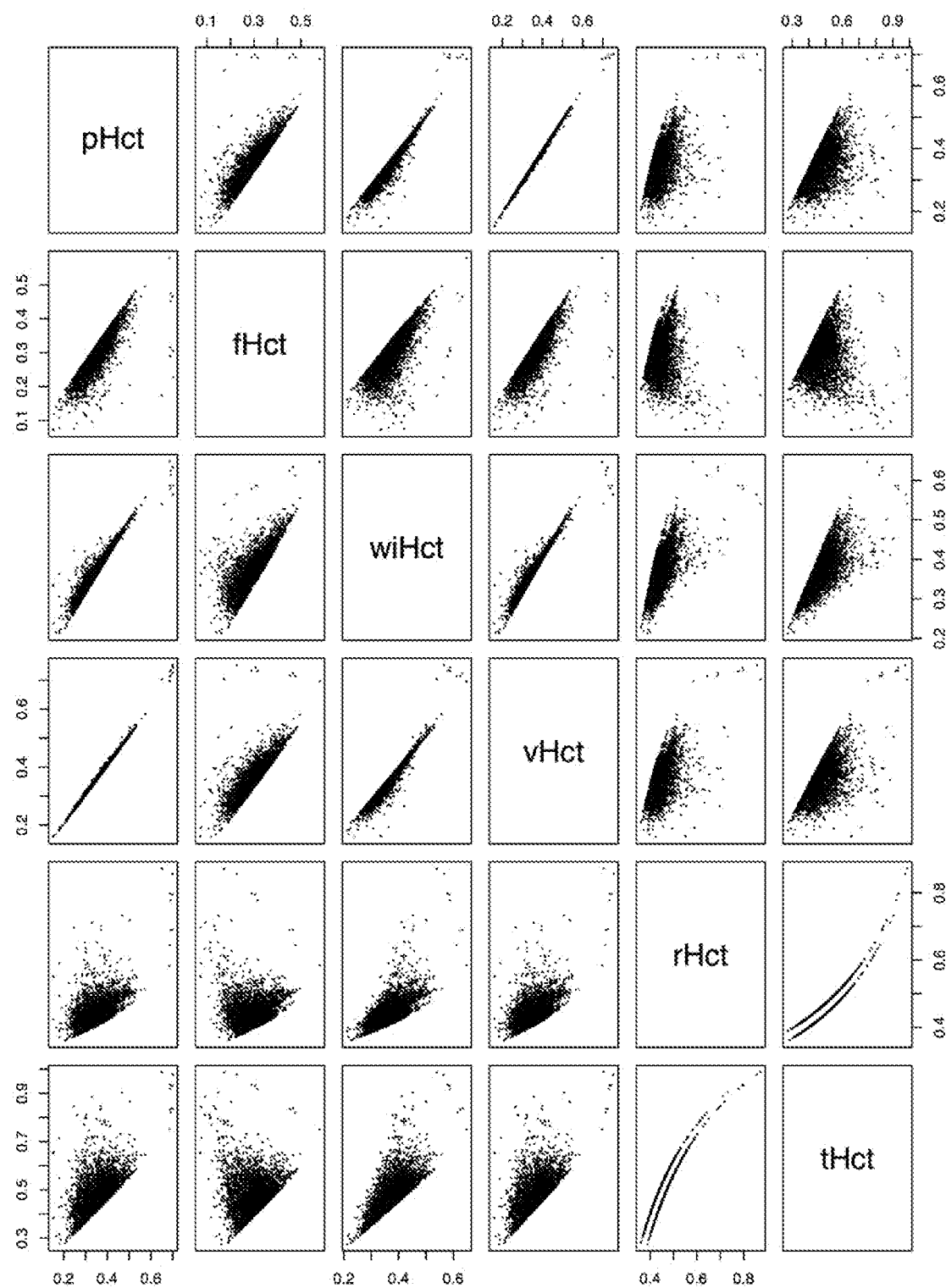
FIG. 6 shows a similar set of scatter plots as in FIG. 1, showing only cases where hypovolemia was present.
Figure 7:
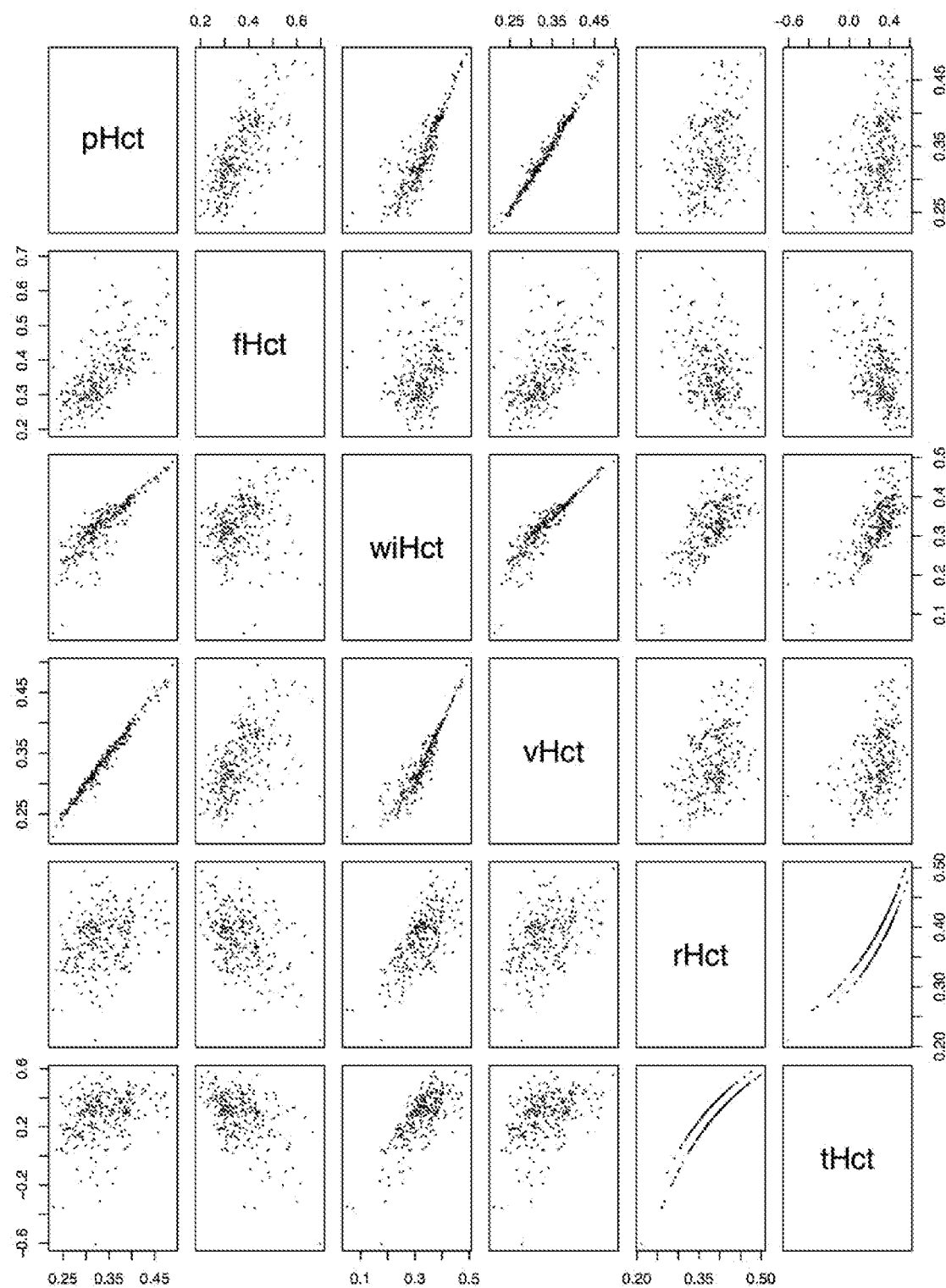
FIG. 7 shows a similar set of scatter plots as in FIG. 1, showing only cases from a study of 250 patients hospitalized with Acute Heart Failure.
Figure 8:
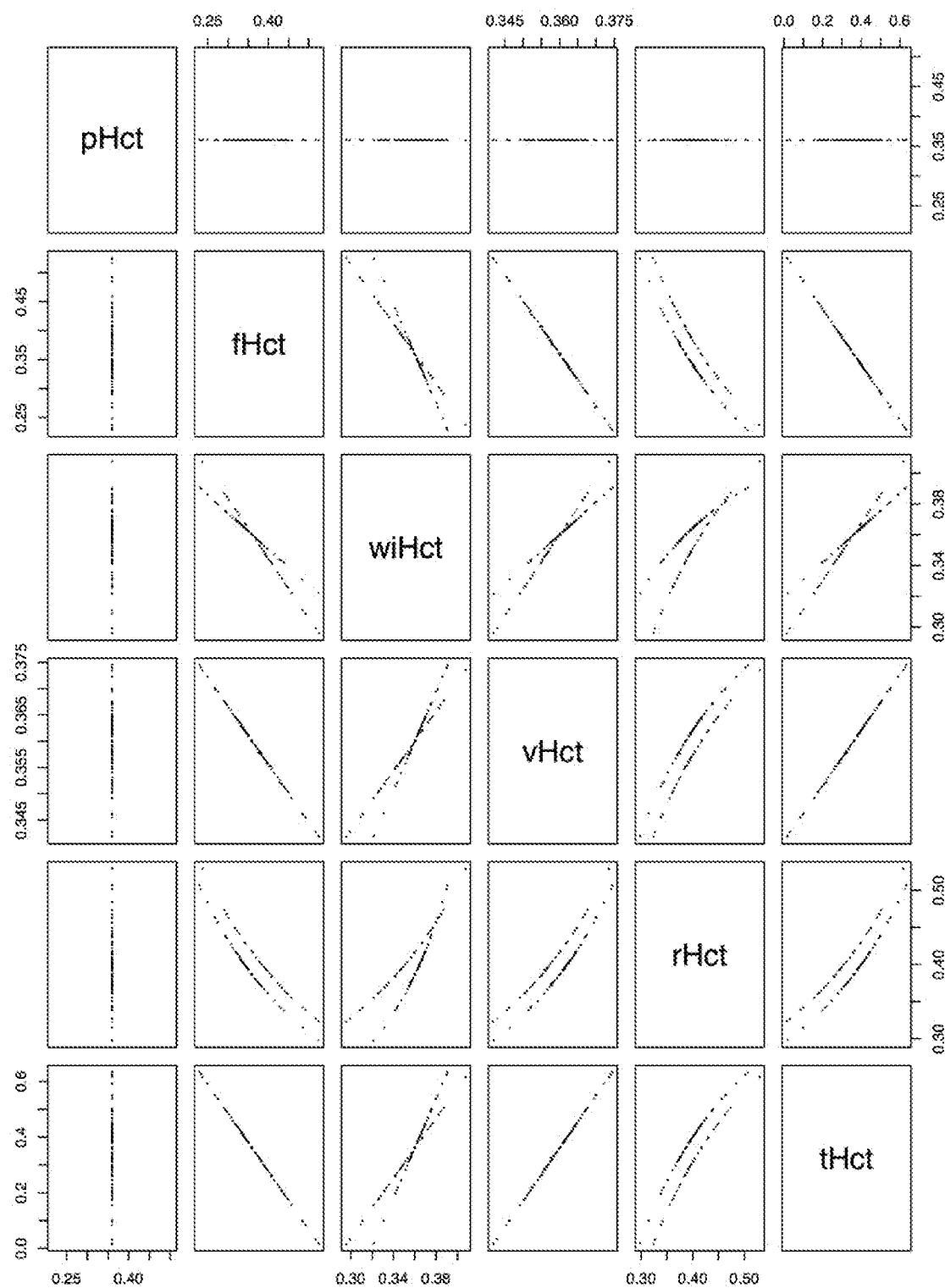
FIG. 8 shows a similar set of scatter plots as in FIG. 1, showing only the 104 cases where pHct was precisely 36.0.

FIG. 5 shows a set of scatter plots of like those in FIG. 1, but only including the 4,890 out of 14,747 cases in which hypervolemia was observed (defined as edrBV>8%). Similarly, FIG. 6 shows a set of scatter plots of like those in FIG. 1, but only including the 9,856 out of 14,747 cases in which hypovolemia was observed (defined as edrBV<−8%). It can be observed that there is still a large amount of heterogeneity present in the relationships of between pHct and the other Hct measures. This indicates that there is a broad spectrum of hypovolemia and hypervolemia, and that the additional Hct measures disclosed herein encode quantitative information beyond the pHct, and also beyond the qualitative fact of hypervolemia or hypovolemia. FIG. 7 shows a set of scatter plots of like those in FIG. 1, but only including 250 cases which were taken from a study of patients hospitalized with Acute Heart Failure. Even within this narrowly defined cohort, it is clear that there is a large amount of heterogeneity, as discussed above. FIG. 8 shows a set of scatter plots of like those in FIG. 1, but only including those 104 out of 14,747 cases in which pHct was measured as precisely 36.0. The heterogeneity observed here is further explored in FIG. 13.

FIG. 9 shows an example of a report showing volume-aware Hct measures for a patient, along with a normal range. The normal range for a male patient would be 38-45%.

FIG. 10 shows a preferred embodiment, in which the volume-aware Hct measures for a patient are displayed as part ("Hematocrit Analysis") of a report that gives the results of the Blood Volume Analysis that was used to calculate the volume-aware Hct measures.

FIG. 11 shows a table of example Volemic States, with notes regarding the application of volume-aware Hematocrit measures.

FIG. 12 shows a sample embodiment of defined reference ranges for volume-aware Hct measures which can be used for producing a report. In this embodiment, seven ranges have been defined, based on deviations from iHct. Note that since iHct is defined as 40% for women and 45% for women, there are separate ranges for men and women. For example: the range (42.75%, 47.25%) is "normal" for men, the range (44%, 46%) is "high" for women, the range (51.75%, 100%) is "very high" for men, the range (0%, 34%) is "very low" for women, etc. In this embodiment, these ranges will be applied to all the volume-aware Hct measures (fHct, rHct, etc.), although different ranges could be specified for each measure. In general, a plurality of numerical ranges may be set for each measure, with values for groups defined by patient characteristic (e.g. gender, age, etc) and conditions (diagnosis, etc.).

FIG. 13 shows a table of data taken from the dataset of 14,747 cases mentioned above. This table shows the 35 male patients who had a measured pHct of precisely 36.0%; it is a subset of the 104 cases including both males and females depicted in FIG. 8. (Note that it is not surprising that there are fewer male than female cases in this subset, as a pHct of 36% is closer to normal for women than it is for men). The heterogeneity of volemic status is quite apparent here, as the patients display a wide range of blood volume abnormalities—e.g. the patient with ID 14707 has a blood volume that is 46% expanded (column edBV), whereas patient 12060 has a blood volume that is 34.1% contracted. Similar examples can be observed for the differences in red cell volume (edRCV) and plasma volume (edPV). Values for five of the volume-aware Hct measures are shown (fHct, $w_iHct$, vHct, rHct, tHct). Selective highlighting has been used on these five columns using some of the reference ranges defined in FIG. 12. Values that fall into the "normal" range are shown in white on a black background; values that fall into the "moderately high" or "moderately low" range are shown in black on a gray background. This highlighting draws attention to the clinical implications of these values. A volume-aware Hct measure in the "normal" or "moderately high/low" ranges can be interpreted as indicative of an appropriate clinical approach to the patient's volume needs.

For example, patient 224 has a low blood volume (−17.6%), but his red cell volume is particularly depleted (−34.1%), whereas his plasma volume is close to normal (−6.4%). The rHct measure is in the normal range, indicating that red cell volume correction via transfusion to achieve normal red cell volume would result in a normal Hct. In contrast, the fHct value of 29.7% shows that a fluid-only correction of his blood volume deficit would result in a more anemic state and is thus contraindicated. Similarly, the $w_iHct$ value of 38.5% shows that a transfusion of whole blood (or of separate red cell and plasma components) to restore him to euvolemia would still leave him with a somewhat low final pHct.

Patient 2401, in contrast, has an expanded blood volume that is caused by a large PV expansion (+29.1%) combined with a mild RCV deficit (−9.1%). The highlighted values show that only the fHct correction is indicated for this patient—removing excess fluid to restore a normal blood volume will leave the patient with a pHct of 40.9%. Patient 4501 shows a similar pattern of volume derangement to patient 2401, but it is interesting to note that none of the last five columns is highlighted. This indicates that only a more complex intervention (i.e. both removing fluid, and adding red cells) will result in a pHct that is close to normal.

A few other details are illuminating to consider. Patient 12060 has a very low blood volume with deficits in both RCV and PV, and the $w_iHct$ value of 40.8% indicates that a balanced whole blood transfusion is indicated. Since all the patients in this table have a low Hct of 36%, venesection never produces a normal or near normal pHct, as venesection does not significantly alter a patient's Hct. A sampling of patients with near-normal Hct but elevated BV would identify candidates for venesection.

FIG. 14 shows a similar table of data to that of FIG. 13, taken from the same dataset of 14,767 cases, showing the 38 patients who had a measured pHct of precisely 45.0%. Highlighting like that of FIG. 13 has been applied, using the range definitions of FIG. 12 (note that the ranges are defined differently for men and women). Because iHct is different for men and women, these male patients all have normal pHct, whereas the female patients all have elevated pHct. Examining the volume excess-deficit columns for the men, it will be noticed that all three values are equal for each patient, a consequence of the fact that iHct=pHct for the men (compare equations (3-5) with equations (7-9)). Among these male patients, however, there is a range of blood volume status from hypovolemic (patient 7177 has edBV of −12.5%) to hypervolemic (patient 10272 has edBV of +54.3%). Treatment indications for the men will be discussed further below in connection with the Hct correction reports in FIGS. 16-22.

The females in FIG. 14 all have elevated RCV to varying degrees, and the highlighting of rHct suggests that for most of these patients, removal of red cells to restore normal red cell volume will result in a near-normal pHct. The exception is patient 3259, who also has an elevated PV; for this patient venesection is more appropriate, as removal of red cells of enough red cells to achieve normal red cell volume without removing fluid as well will leave the patient slightly anemic, indicated by the rHct value of 35.9%.

FIG. 15 shows a table of the various Hct measures disclosed herein, showing the volume that is targeted and sample treatments that might be used to achieve the target. For example, fHct targets the Ideal Blood Volume by adding or subtracting fluids. Treatments to add fluids include Plasma transfusion, albumin transfusion, IV fluids, oral rehydration, etc. Treatments to remove fluids include loop and other diuretics, ultrafiltration, plasmapheresis, etc. Additive treatments involving fHct will result in a decrease in the observed pHct, as there will be more PV while RCV stays constant. Note that aHct differs from fHct only in that Ideal Plasma Volume is the target rather than Ideal Blood Volume. Similarly, tHct differs from rHct only in that Ideal Red Cell Volume is the target rather than Ideal Blood Volume. The row for iHct is shown by way of contrast—since iHct is a fixed quantity (45% for men, 40% for women) the iHct correction involves restoring both PV and RCV to their ideal values (and thus BV to its ideal value). This will typically require changes both in fluids and in red cells.

FIGS. 16-22 show sample Hct correction reports generated by a preferred embodiment of the invention. FIGS. 16-18 provide details on cases shown in the table in FIG. 13, and FIGS. 19-22 provide details on cases shown in the table in FIG. 14. Each panel (e.g. the upper panel in FIG. 16 contains information on Patient 224) contains a three-line summary of the of the volemic status of the patient, along with descriptive text based on pre-defined ranges. For example, for patient 224, his Blood volume is contracted by 1117 ml from the Ideal Value for him, which is characterized as a "moderate deficit". The ranges for these values are defined in the "Blood Volume Analysis Results" panel of FIG. 10. The table below the volemic summary gives a detailed view of the corrected Hct measures, relating the measures to the potential interventions that they represent. The first line displays pHct, the current measured peripheral Hct. The next line displays iHct, and all subsequent lines represent the interventions that are applicable for that patient based on volemic status—interventions marked as "Not applicable" in the table of FIG. 15 are omitted. To be more specific, for a given patient, for each measure, the deviation of the relevant Ideal Volume Target (either Blood Volume, Plasma Volume, or Red Cell Volume) is determined; a positive deviation (meaning that the patient value is higher than the ideal value) corresponds to a removal treatment. For patient 224, all the deviations are negative, so only additive treatments are considered, and vHct, rHct, and tHct are omitted from the report. (In contrast, patient 14383 in FIG. 18 has all positive deviations, and $w_r$Hct, $w_{70}$Hct, and $r_{70}$Hct are omitted from the report.) The "Status" column displays a descriptive text for each measure, as defined by the ranges in FIG. 12. The "Intervention" column specifies and quantifies the interventions that correspond to each Hct measure. The "Volume Target" column specifies which ideal volume measure is the target of the intervention. The iHct measure, which is defined as a constant of 40% for women and 45% for men, is associated with two corrections: both fluids and red cells. All the the other Hct measures are associated with a single correction. For patient 224, the addition of 241 ml of fluids and the addition of 876 ml of red cells will result in ideal values for Plasma Volume and Red Cell Volume, and thus of Blood Volume. The $r_{70}$Hct and $w_{70}$Hct lines show that these interventions will result in Hct measures that are in the "normal" range. In contrast, the following three interventions all will result in Hct measures that either LOW or VERY LOW. Note that the interventions are displayed in order of their closeness to the iHct value, and that a dividing line has been used to visually separate the interventions that are in the "normal" range. This provides immediate visual feedback on the appropriateness of contemplated interventions. For patient 224, transfusion of an appropriate quantity of packed red cells would result in a normal Hct; restoring the patient's blood volume with fluids alone would result in an even lower Hct of 29.7%. In this instance, the fHct can also be interpreted as a measure of the consequences of non-intervention with a transfusion. The patient has a measured pHct of 36%, but the patient's anemia is actually more severe than that number would indicate, because there has been incomplete fluid compensation; if the fluids were restored (i.e. fully compensated) then the resulting Hct would actually be 29.7%.

Patient 2401 (bottom panel in FIG. 16) also has a pHct of 36%, but his volume status is very different, with a mild hypervolemia composed of a severe excess of plasma volume, and a "normal deficit" of red cell volume. This type of volume profile is typically seen with congestive heart failure. The table of Hct corrections shows that none of the single-modality corrections (i.e. those associated with anything other than iHct) result in a "normal" Hct value. This is highlighted by the fact that all of them are listed "below the line". The corrections that come closest to restoring a normal Hct are aHct, which would remove all the excess plasma volume, and fHct, which would remove only enough plasma to achieve the ideal blood volume—i.e. some extra plasma would remain, compensating for the red cell volume deficit, and resulting in a lower Hct.

This patient case is also illustrative in the use of the Hct corrections information in guiding treatment by providing Hct "targets". Vascular fluid is in a relatively fast, complex dynamic equilibrium with non-vascular fluid. Addition and removal treatments such as those listed in the fHct/aHct row of FIG. 15 can generally not be directly and precisely quantified in terms of their impact on circulatory plasma volume. For example, transfusion of fluids directly into the vascular system does not result in a sustained increase in plasma volume of the full volume of the transfusion. Similarly, removal of a given volume of fluids from the vascular system by ultrafiltration does not result in a drop in plasma volume of the full volume removed. In both cases the extra-vascular fluid changes as well. Since the production or loss (in the absence of significant bleeding) of red cells is much slower than the rate of fluid compensation, the pHct can be used to monitor the progress of the treatment. In the case of patient 2401, a plasma removal treatment could have as its "target" a pHct of 40.9% (equal to the fHct), with the aim of insuring that the patient's blood volume was not taken below normal levels. Using the aHct of 42.5% would restore the ideal plasma volume, and leave the patient slightly hypovolemic. Both of these are rather more conservative than attempting to restore the patient to a "normal" Hct of 45% using fluid correction alone.

In a preferred embodiment, an automated treatment modality such as an ultrafiltration machine is connected to or outfitted with a real-time Hct monitor, which halts treatment when a target corrected Hct measure such as aHct or fHct is achieved. In one embodiment, the target is chosen to be the first threshold to be reached among iHct, aHct, and fHct.

Patient 4501 (top panel in FIG. 17) is similar to patient 2401, with a slightly more pronounced anemia; this has the effect that the fHct value is now LOW rather than moderately low. Patient 8767 (lower panel in FIG. 17), in contrast, has a hypervolemia which is wholly attributable to excess plasma volume. This patient would likely benefit from more aggressive fluid removal treatment to achieve a normal Hct of 45%. Patient 12060 (top panel in FIG. 18) has an extreme deficit of blood volume, perhaps from trauma or surgery. None of the individual corrections alone will restore a normal Hct, but the presence of $r_{70}$Hct at the top of the list suggests the clear need for a blood transfusion; such a patient is extremely likely to be receiving IV fluids as well as a matter of course. The last line of the corrections report, showing a VERY LOW value for the fHct provides an important quantification (and perhaps caution) of the consequence of restoring blood volume only with fluids—the peripheral Hct will be 23.7% if no red cells are given.

Patient 14383 (lower panel in FIG. 18) has hypervolemia with an excess of both red cells and plasma, as might be seen in heart failure or Polycythemia Vera. The correction report shows that a restoring normal plasma volume or normal blood volume require MORE aggressive targets (aHct=47.1%, fHct=48.6% respectively) than just the "normal" male Hct value of 45%.

FIGS. 19 and 20 present three illustrative cases from the table in FIG. 14. These three male patients have the "normal" pHct value of 45%, resulting from the fact that the percentage deviations of their plasma and red cells are identical, but the patients exhibit very different volemic status. Patient 7177 (top panel in FIG. 19) is hypovolemic. The Hct corrections report shows $w_iHct=45.6\%$, indicating that a transfusion containing both plasma and red cells (perhaps autologous blood stored before a surgery) would restore normal blood volume. Patient 5173 (lower panel in FIG. 19) has near-normal values for blood volume, plasma volume, and red cell volume. The "Status" entry for his pHct line is "normal Hct & volumes", suggesting that no volume correction is needed. Patient 10272 (FIG. 20) is hypervolemic. The corrections report indicates that venesection (removal of whole blood) will result in a near-normal Hct. Note that the vHct=42.3% is an example of the effect of Hct being lowered slightly by venesection as discussed above. The final venesection corrected peripheral Hct ($v_fHct$) will be in the range [42.3%, 45%] as shown in Equation (27).

FIGS. 21 and 22 present three illustrative female cases from the table in FIG. 14. These three patients also have a pHct value of 45%, but since they are women this is a HIGH value for them. Patient 3259 (top panel in FIG. 21) is severely hypervolemic, with uneven excess of plasma and red cells. The correction report suggests that a combination therapy dealing with both fluids and red cells will likely be needed. The venesection line at the top of the non-ideal interventions indicates that this will result in the closest to normal Hct. The rHct and tHct lines suggest that fully removing the excess of red cells will leave the patient with a LOW or VERY LOW Hct. The aHct and fHct lines suggest that fully removing the excess of fluids will leave the patient with a HIGH or VERY HIGH Hct.

In a preferred embodiment, an automated treatment modality such as an erythrocytapheresis machine is connected to or outfitted with a real-time Hct monitor, which halts treatment when a target corrected Hct measure such as rHct or tHct is achieved. In one embodiment, the target is chosen to be the first threshold to be reached among iHct, rHct, and tHct.

Patient 3907 (lower panel in FIG. 21) has a mixed volemic status, with a small excess of red cells. Although this patient's mild volume derangement might not merit treatment, the various Hct measures provide possible target values. Patient 3513 (FIG. 22) has a red cell excess, with a very small plasma deficit. The normal rHct of 40.8% suggests the possible intervention of red cell removal, with a target of 40.8%, slightly higher than the "normal" value of 40%.

What is claimed is:

1. A system for automatically analyzing blood of a human patient, comprising a concentration counter configured to analyze one or more samples of blood or plasma, a user interface operatively connected to the concentration counter and configured for entry and display of information, a memory, one or more processors operatively coupled to the memory and programmed instructions stored in the memory, wherein the instructions are configured to carry out a method comprising the steps of:

a) gathering data, from the concentration counter, about the concentration of a tracer within the one or more samples of blood or plasma from the human patient;

b) calculating, by the one or more processors, a blood volume (BV), plasma volume (PV), and red cell volume (RCV) for the patient;

c) calculating, by the one or more processors, an ideal blood volume (iBV), ideal plasma volume (iPV), and red cell volume (iRCV) for the patient based on previously collected patient descriptive data such as height, weight, and gender;

d) calculating, by the one or more processors, a fluid corrected Hct (fHct) defined to be the peripheral Hct that would be observed, if the patient's plasma volume were adjusted so that the patient's blood volume is the Ideal Blood Volume;

e) calculating, by the one or more processors, one or more of the following values:

i) plasma volume corrected Hct (aHct), which is defined to be the peripheral Hct that would be observed if the patient's plasma volume were adjusted so that the patient's Plasma Volume is the Ideal Plasma Volume;

ii) whole blood corrected Hematocrit ($w_bHct$), which is defined to be the peripheral Hct that would be observed if the patient were given, or had removed, whole blood with a red cell to plasma ratio of bHct, so that the patient's blood volume is the Ideal Blood Volume;

iii) whole blood ideal corrected Hematocrit ($w_iHct$), which is defined as the whole blood corrected Hematocrit ($w_bHct$) where bHct is the ideal Hct for the patient;

iv) whole blood corrected Hct obtained when correcting the patient's total blood volume using packed red cells ($w_{70}Hct$);

v) venesection corrected Hct (vHct), defined to be the peripheral Hct (pHct) that would be observed if the patient had blood removed to achieve Ideal Blood Volume, together with a final venesection corrected peripheral Hct range defined to be the peripheral Hct that would be observed after a venesection was performed over a time period allowing for fluid compensation, calculated as [vHct, pHct];

vi) red cell volume corrected Hematocrit (rHct), defined to be the peripheral Hct that would be observed if the patient had removed red blood cells so that the patient's red blood cell volume is the Ideal Red Blood Cell Volume;

vii) packed red cell volume corrected Hematocrit ($r_{70}Hct$), defined to be the peripheral Hct that would be observed if the patient were given red blood cells so that the patient's red blood cell volume is the Ideal Red Blood Cell Volume, taking into account the typical 70% Hct of packed red cells; and viii) red cell total blood volume corrected Hematocrit (tHct), defined to be the peripheral Hct that would be observed, if the patient had removed red blood cells so that the patient's total blood cell volume is the Ideal Blood Volume;

f) displaying, by the one or more processors, at the user interface, one or more of the one or more values calculated in step (e) so as to provide an analysis of the one or more samples of blood or plasma; and g) guiding a method of treatment of the patient for a blood volume abnormality based on the analysis of the samples of blood or plasma;

wherein in step (a) the tracer is a radioactive isotope, and the counter is a radiation counter equipped with one or more counting wells, with or without a mechanism for moving samples into counting wells, or the tracer is a light-emitting or light-absorbent tracer, and the counter is capable of measuring light emission or absorption either in multiple samples conveyed to the counter, or by direct measurement of circulating patient blood and wherein the treatment of the patient for a blood volume abnormality comprises one or more of: transfusion of one or more blood components to the patient, ultrafiltration of the patient's blood to remove excess fluid from the blood, phlebotomy, administration of a diuretic to the patient or adjusting a dose of a diuretic administered to the patient, and erythrocytapheresis of the patient's blood.

2. The system of claim 1, where the tracer is a radioactive isotope, and the counter is a radiation counter equipped with one or more counting wells, with or without a mechanism for moving samples into counting wells.

3. The system of claim 1, where the tracer is a light-emitting (optionally fluorescent) tracer or a light-absorbent tracer (optionally a dye), and the counter is capable of measuring light emission or absorption either in multiple samples conveyed to the counter, or by direct measurement of circulating patient blood.

4. The system of claim 1, further comprising calculating euvolemic concentration correction factors for whole blood and/or plasma.

5. The system of claim 4, where one or both of the following are calculated:
euvolemic Hemoglobin concentration, and
euvolemic Albumin concentration.

6. The system of claim 4, where a plurality of patient concentrations are entered into the processor and a report is generated comparing euvolemic values for each concentration to standard reference ranges for each concentration.

7. The system of claim 1, where a report is generated listing corrected Hct values for the patient, along with a normal range.

8. The system of claim 7, where a report is generated listing and quantifying interventions associated with each corrected Hct value.

9. The system of claim 8, where a description based on reference ranges is associated with each intervention.

10. The system of claim 8, where the interventions are listed in the report in order of suitability, defined by distance of Hct measure from an ideal Hct (iHct).

11. The system of claim 8, where formatting of the report is used to distinguish interventions.

12. The system of claim 7, where one or more corrected Hct values are used as a target value for an intervention aimed at establishing an ideal blood volume for the patient.

13. The system of claim 12, where the intervention is ultrafiltration, aHct is calculated, and the target value is a function of aHct, fHct, and/or an ideal Hct (iHct).

14. The system of claim 12, where the intervention is ultrafiltration, and a continuous, real-time measurement of Hct is incorporated into the system to automatically terminate the intervention when the target value is reached.

15. The system of claim 12, where the intervention is erythrocytapheresis, rHct and tHct are calculated, and the target value is a function of rHct, tHct, and/or an ideal Hct (iHct).

16. The system of claim 12, where the intervention is erythrocytapheresis, and a continuous, real-time measurement of Hct is incorporated into the system to automatically terminate the intervention when the target value is reached.

17. A method of treating a patient for a blood, plasma, or red-cell volume abnormality, the method comprising:

A) receiving an analysis of the patient's blood by a system for automatically analyzing blood of a human patient, the system comprising a concentration counter configured to analyze one or more samples of blood or plasma, a user interface operatively connected to the concentration counter and configured for entry and display of information, a memory, one or more processors operatively coupled to the memory and programmed instructions stored in the memory, wherein the instructions are configured to carry out a method comprising the steps of:

a) gathering data, from the concentration counter, about the concentration of a tracer within the one or more samples of blood or plasma from the human patient b) calculating, by the one or more processors, a blood volume (BV), plasma volume (PV), and red cell volume (RCV) for the patient;

c) calculating, by the one or more processors, an ideal blood volume (iBV), ideal plasma volume (iPV), and ideal red cell volume (iRCV) for the patient based on previously collected patient descriptive data such as height, weight, and gender;

d) calculating, by the one or more processors, a fluid corrected Hct (fHct) defined to be the peripheral Hct that would be observed, if the patient's plasma volume were adjusted so that the patient's blood volume is the Ideal Blood Volume;

e) calculating, by the one or more processors, one or more of the following values:

i) plasma volume corrected Hct (aHct), which is defined to be the peripheral Hct that would be observed if the patient's plasma volume were adjusted so that the patient's Plasma Volume is the Ideal Plasma Volume;

ii) whole blood corrected Hematocrit ($w_b$Hct), which is defined to be the peripheral Hct that would be observed if the patient were given, or had removed, whole blood with a red cell to plasma ratio of bHct, so that the patient's blood volume is the Ideal Blood Volume;

iii) whole blood ideal corrected Hematocrit ($w_i$Hct), which is defined as the whole blood corrected Hematocrit ($w_b$Hct) where bHct is the ideal Hct for the patient;

iv) whole blood corrected Hct obtained when correcting the patient's total blood volume using packed red cells ($w_{70}$Hct);

v) venesection corrected Hct (vHct), defined to be the peripheral Hct (pHct) that would be observed if the patient had blood removed to achieve Ideal Blood Volume, together with a final venesection corrected peripheral Hct range defined to be the peripheral Hct that would be observed after a venesection was performed over a time period allowing for fluid compensation, calculated as [vHct, pHct];

vi) red cell volume corrected Hematocrit (rHct), defined to be the peripheral Hct that would be observed if the patient had removed red blood cells so that the patient's red blood cell volume is the Ideal Red Blood Cell Volume;

vii) packed red cell volume corrected Hematocrit ($r_{70}$Hct), defined to be the peripheral Hct that would be observed if the patient were given red blood cells so that the patient's red blood cell volume is the Ideal Red Blood Cell Volume, taking into account the typical 70% Hct of packed red cells; and viii) red cell total blood volume corrected Hematocrit (tHct), defined to be the peripheral Hct that would be observed, if the patient had removed red blood cells so that the patient's total blood cell volume is the Ideal Blood Volume; and f) displaying, by the one or more processors, at the user interface, one or more of the one or more values calculated in step (e) so as to provide an analysis of the one or more samples of blood or plasma; and B) selecting a treatment for the patient's abnormality based on the received analysis of the patient's blood and administering the treatment to the patient, wherein the treatment of the patient for the abnormality comprises one or more of:

transfusion of one or more blood components to the patient;

ultrafiltration of the patient's blood to remove excess fluid from the blood;

phlebotomy;

administration of a diuretic to the patient or adjusting a dose of a diuretic administered to the patient; and erythrocytapheresis of the patient's blood.

18. The method of treatment of claim 17, where the treatment is ultrafiltration of the patient's blood, and ultrafliltration is continued until a target Hct is reached, said target value being determined as a function of fHct, aHct, and/or an ideal Hct (iHct).

19. The method of treatment of claim 17, where the treatment is erythrocytapheresis of the patient's blood, and erythrocytapheresis is continued until a target Hct is reached, said target value being determined as a function of fHct, aHct, and/or an ideal Hct (iHct).

20. The method of claim 17, wherein in step (a)

the tracer is a radioactive isotope, and the counter is a radiation counter equipped with one or more counting wells, with or without a mechanism for moving samples into counting wells, or the tracer is a light-emitting or light-absorbent tracer, and the counter is capable of measuring light emission or absorption either in multiple samples conveyed to the counter, or by direct measurement of circulating patient blood.

* * * * *